(12) United States Patent
Sano et al.

(10) Patent No.: US 12,079,633 B2
(45) Date of Patent: Sep. 3, 2024

(54) TASK EXECUTION ORDER DETERMINATION SYSTEM AND TASK EXECUTION METHOD

(71) Applicant: Maxell, Ltd., Kyoto (JP)

(72) Inventors: Yuko Sano, Tokyo (JP); Akihiko Kandori, Tokyo (JP); Mitsunobu Watanabe, Oyamazaki (JP)

(73) Assignee: Maxell, Ltd., Kyoto (JP)

( * ) Notice: Subject to any disclaimer, the term of this patent is extended or adjusted under 35 U.S.C. 154(b) by 0 days.

(21) Appl. No.: 17/885,918

(22) Filed: Aug. 11, 2022

(65) Prior Publication Data

US 2022/0382554 A1 Dec. 1, 2022

Related U.S. Application Data

(63) Continuation of application No. 16/313,483, filed as application No. PCT/JP2017/034729 on Sep. 26, 2017, now abandoned.

(30) Foreign Application Priority Data

Sep. 29, 2016 (JP) .................................. 2016-191129

(51) Int. Cl.
*G06F 9/38* (2018.01)
*A61B 5/00* (2006.01)
(Continued)

(52) U.S. Cl.
CPC .......... *G06F 9/3856* (2023.08); *A61B 5/7275* (2013.01); *G06F 3/011* (2013.01);
(Continued)

(58) Field of Classification Search
CPC ........ G06F 9/3855; G06F 3/011; G06F 3/017; G06F 9/30094; G06F 9/48; A61B 5/7275
See application file for complete search history.

(56) References Cited

U.S. PATENT DOCUMENTS

| | | | |
|---|---|---|---|
| 2005/0187436 A1* | 8/2005 | Doniger | A61B 5/16 128/920 |
| 2011/0054361 A1* | 3/2011 | Sakoda | A61B 5/4082 600/595 |

(Continued)

FOREIGN PATENT DOCUMENTS

| | | |
|---|---|---|
| JP | 2011-045520 A | 3/2011 |
| JP | 2015-217282 A | 12/2015 |

(Continued)

OTHER PUBLICATIONS

Montreal Cognitive Assessment andMini-Mental State Examination are bothvalid cognitive tools in stroke; Cummin et el.; 2013 (Year: 2013).*

(Continued)

*Primary Examiner* — Deirdre D Hatcher
(74) *Attorney, Agent, or Firm* — Mattingly & Malur, PC

(57) ABSTRACT

A technique for evaluating human cognitive and motor functions by a plurality of hand movement tasks is disclosed. A task execution method determines the execution order of a plurality of tasks which a test subject is caused to execute to acquire a characteristic quantity. A test subject group task database includes scores given in advance and characteristic quantities obtained from a plurality of tasks stored as past data corresponding to each of a plurality of test subjects. In a storage device, (1) a differentiation precision database for a case in which test subjects are divided into two groups by predetermined threshold value scores differentiated by the characteristic quantities, or (2) an estimation precision database for a case in which a score is estimated using the characteristic quantity for a predetermined score value is prepared for each of the tasks on the basis of the test subject group task database.

5 Claims, 27 Drawing Sheets

(51) Int. Cl.
*G06F 3/01* (2006.01)
*G06F 9/30* (2018.01)
*G06F 9/48* (2006.01)

(52) U.S. Cl.
CPC .......... *G06F 3/017* (2013.01); *G06F 9/30094* (2013.01); *G06F 9/48* (2013.01)

(56) References Cited

U.S. PATENT DOCUMENTS

| | | |
|---|---|---|
| 2013/0018592 A1 | 1/2013 | Mollicone |
| 2013/0224117 A1 | 8/2013 | Royall |
| 2014/0040905 A1 | 2/2014 | Tsunoda |
| 2015/0126899 A1 | 5/2015 | Ghajar |
| 2016/0100788 A1 | 4/2016 | Sano et al. |
| 2016/0262680 A1 | 9/2016 | Martucci |
| 2016/0307145 A1 | 10/2016 | Banerjee |
| 2017/0251956 A1 | 9/2017 | Kandori et al. |
| 2017/0344921 A1 | 11/2017 | Leonelli |

FOREIGN PATENT DOCUMENTS

| | | |
|---|---|---|
| WO | 2015/037089 A1 | 3/2015 |
| WO | 2016/031348 A1 | 3/2016 |

OTHER PUBLICATIONS

A neuropsychological battery to detect specific executive and social cognitive impairments in early frontotemporal dementia; Torralva et al.; 2009 (Year: 2009).*

International Search Report of PCT/JP2017/034729 dated Oct. 31, 2017.

Quantitative magnetic detection of finger movements in patients with Parkinson's disease; Kandori; Mar. 2004 (Year: 2004).

Defining optimal cutoff scores for cognitive impairment using MDS Task Force PD-MCI criteria; Goldman et al.; Dec. 2013 (Year: 2013).

Montreal Cognitive Assessment for the diagnosis of Alzheimer's disease and other dementias; Davis et al.; Oct. 2015 (Year: 2015).

* cited by examiner

F I G. 1
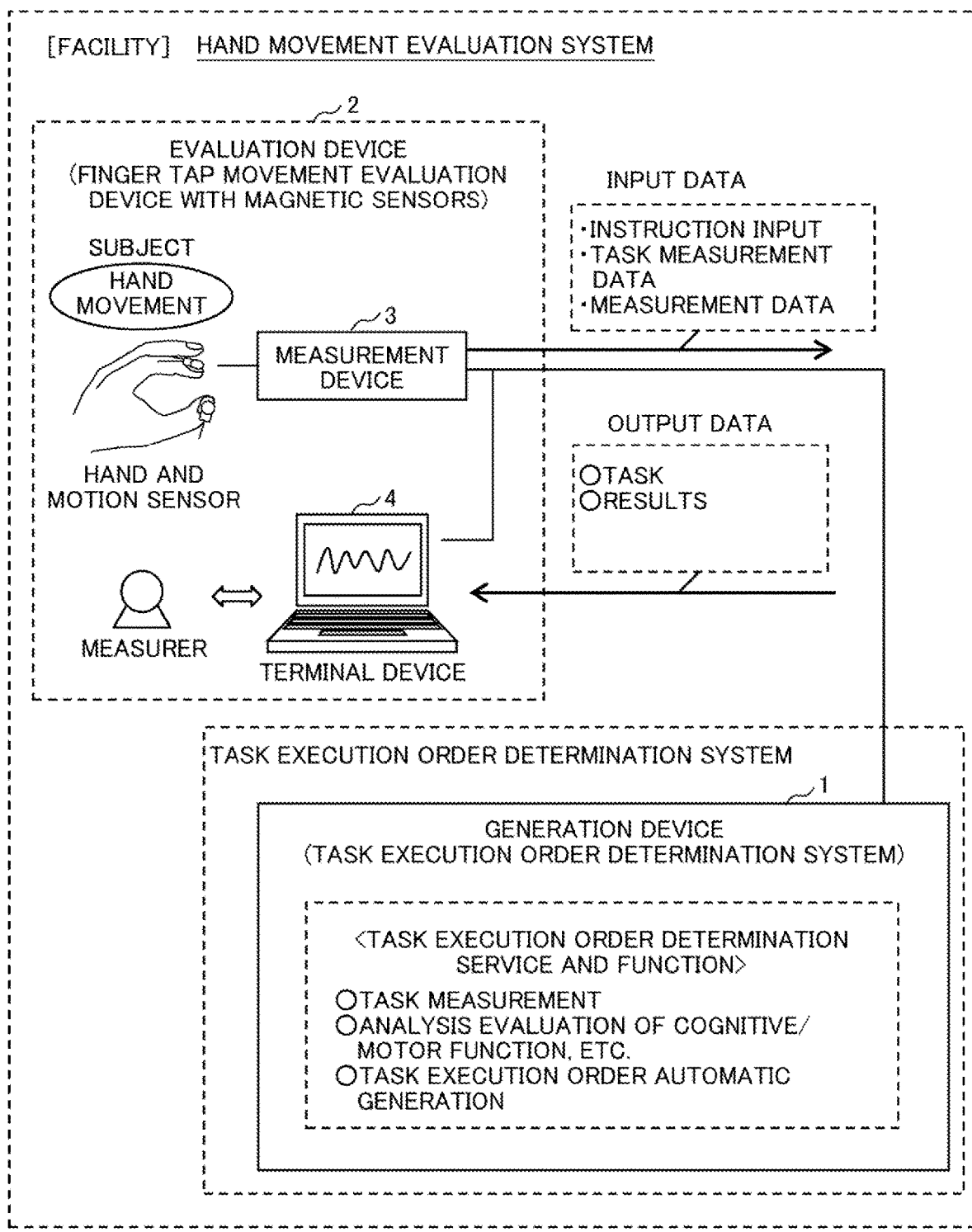

FIG. 7
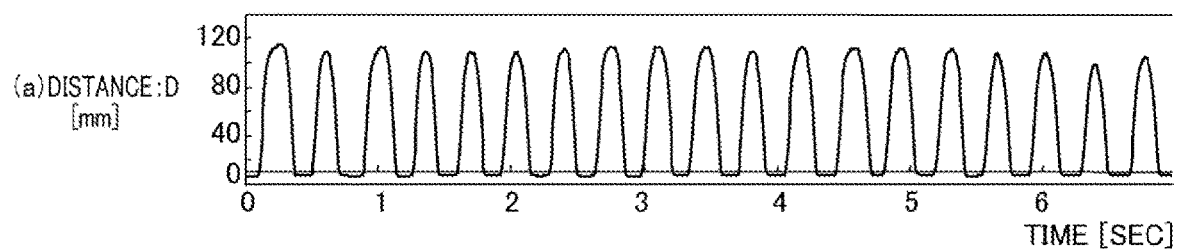
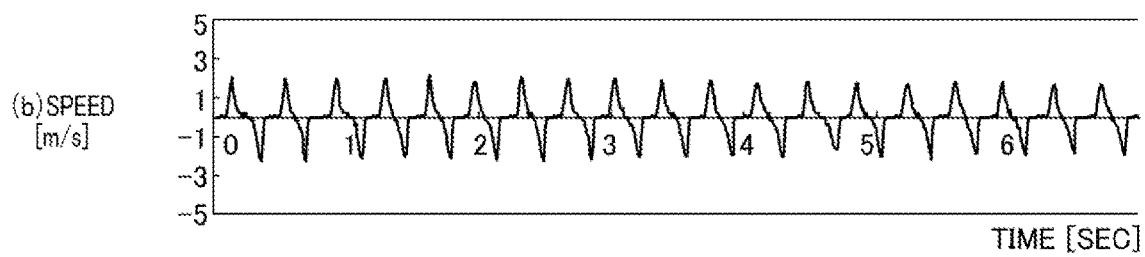
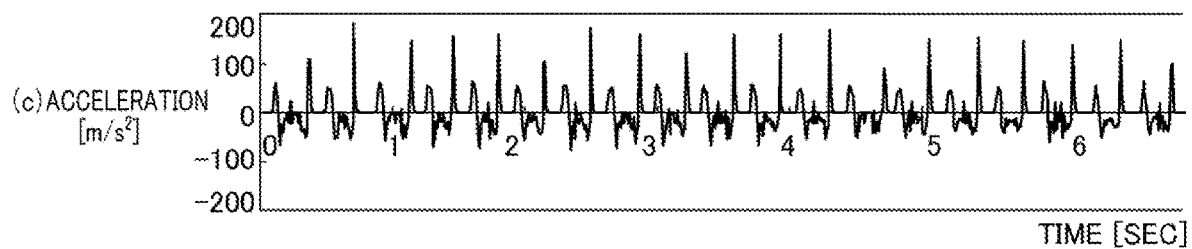
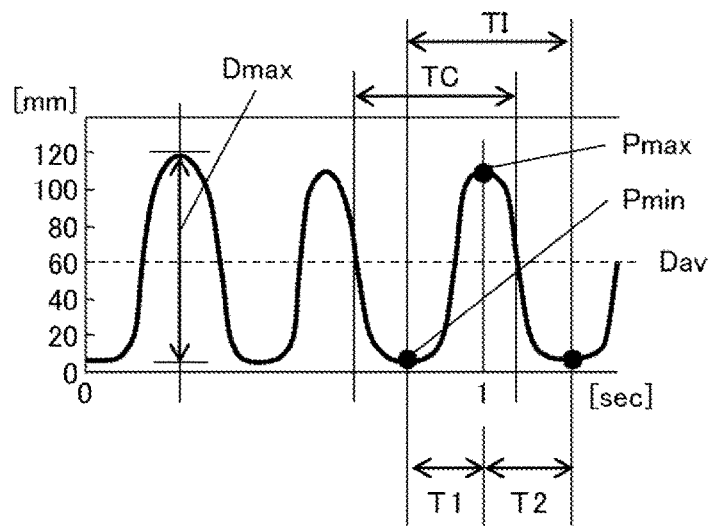

| CHARACTERISTIC QUANTITY CLASSIFICATION | IDENTIFICATION NUMBER | CHARACTERISTIC QUANTITY PARAMETER [UNIT] |
|---|---|---|
| DISTANCE | 1 | MAXIMUM AMPLITUDE OF DISTANCE [mm] |
| | 2 | TOTAL MOVEMENT DISTANCE [mm] |
| | 3 | AVERAGE OF MAXIMUM POINT OF DISTANCE [mm] |
| | 4 | STANDARD DEVIATION OF MAXIMUM POINT OF DISTANCE [mm] |
| | 5 | SLOPE OF APPROXIMATE LINE OF MAXIMUM POINT OF DISTANCE (DECAY RATE) [mm/sec] |
| | 6 | VARIATION COEFFICIENT OF MAXIMUM POINT OF DISTANCE [-] |
| | 7 | STANDARD DEVIATION OF LOCAL MAXIMUM POINT OF DISTANCE [mm] |
| ... | ... | ... |

F I G. 1 0 A
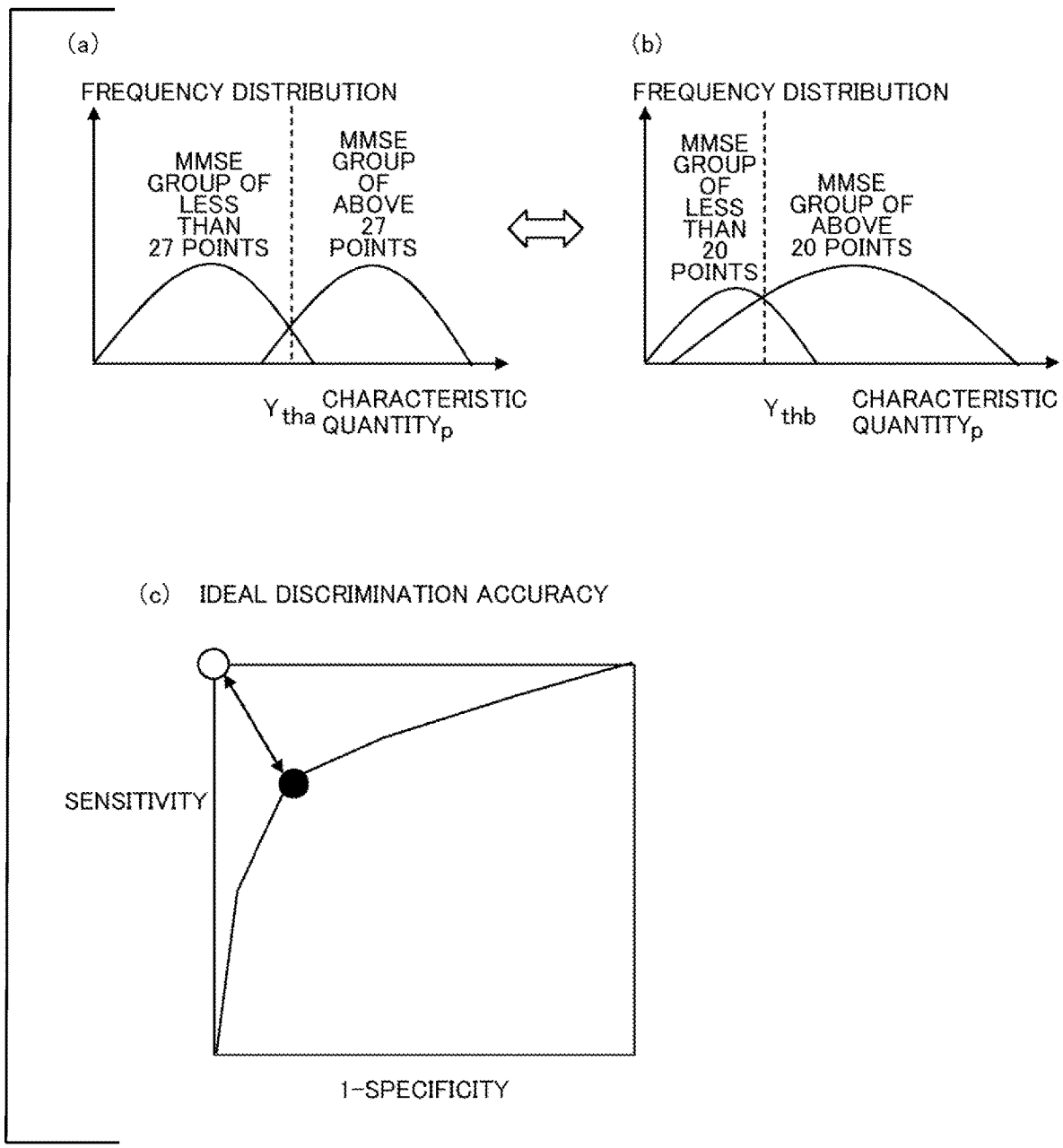

F I G. 1 0 C

| TASK | THRESHOLD OF MMSE N | DISCRIMINATION ACCURACY (AUC) | FORMULA OF DISCRIMINATION INDEX | THRESHOLD OF DISCRIMINATION INDEX | SEVERITY DIRECTION |
|---|---|---|---|---|---|
| ONE HAND METRONOME | 29 | 0.15 | $Y = A_{10}X_0 + A_{11}X_1 + A_{12}X_2 + ...$ | $Y_{th29}$ | 1 |
| ONE HAND METRONOME | 28 | 0.30 | $Y = A_{10}X_0 + A_{11}X_1 + A_{12}X_2 + ...$ | $Y_{th28}$ | 1 |
| ONE HAND METRONOME | 27 | 0.62 | $Y = A_{10}X_0 + A_{11}X_1 + A_{12}X_2 + ...$ | $Y_{th27}$ | 1 |
| ONE HAND METRONOME | 26 | 0.44 | $Y = A_{10}X_0 + A_{11}X_1 + A_{12}X_2 + ...$ | $Y_{th26}$ | 1 |
| ONE HAND METRONOME | ... | ... | ... | ... | ... |
| ONE HAND METRONOME | ... | ... | ... | ... | ... |
| ONE HAND METRONOME | 1 | 0.02 | $Y = A_{10}X_0 + A_{11}X_1 + A_{12}X_2 + ...$ | $Y_{th1}$ | −1 |

MILD ←→ SEVERE

| TASK | THRESHOLD OF MMSE $N_{max}$ | DISCRIMINATION ACCURACY (AUC) | FORMULA OF DISCRIMINATION INDEX | THRESHOLD OF DISCRIMINATION INDEX | SEVERITY DIRECTION |
|---|---|---|---|---|---|
| ONE HAND METRONOME | 27 | 0.62 | $Y = A_{10}X_0 + A_{11}X_1 + A_{12}X_2 + ...$ | $Y_{th1A}$ | 1 |
| BOTH HAND ALTERNATE FREE RUN | 22 | 0.76 | $Y = A_{20}X_0 + A_{21}X_1 + A_{22}X_2 + ...$ | $Y_{th2A}$ | -1 |
| BOTH HAND SIMULTANEOUS FREE RUN | 17 | 0.76 | $Y = A_{30}X_0 + A_{31}X_1 + A_{32}X_2 + ...$ | $Y_{th3A}$ | -1 |
| ONE HAND FREE RUN | 15 | 0.72 | $Y = A_{40}X_0 + A_{41}X_1 + A_{42}X_2 + ...$ | $Y_{th4A}$ | 1 |

MILD ↔ SEVERE

| TASK | VALUE OF MMSE Nmax | REGRESSION ACCURACY (MEAN SQUARE ERROR) | FORMULA OF REGRESSION INDEX | THRESHOLD OF DISCRIMINATION INDEX | SEVERITY DIRECTION |
|---|---|---|---|---|---|
| ONE HAND METRONOME | 28 | 1.2 | $Y = A_{10}X_0 + A_{11}X_1 + A_{12}X_2 + \ldots$ | $Y_{th1B}$ | 1 |
| BOTH HAND ALTERNATE FREE RUN | 23 | 1.5 | $Y = A_{20}X_0 + A_{21}X_1 + A_{22}X_2 + \ldots$ | $Y_{th2B}$ | −1 |
| BOTH HAND SIMULTANEOUS FREE RUN | 18 | 1.3 | $Y = A_{30}X_0 + A_{31}X_1 + A_{32}X_2 + \ldots$ | $Y_{th3B}$ | −1 |
| ONE HAND FREE RUN | 14 | 0.8 | $Y = A_{40}X_0 + A_{41}X_1 + A_{42}X_2 + \ldots$ | $Y_{th4B}$ | 1 |

MILD ↔ SEVERE

```
EVALUATION RESULT (FOR MEASURER)            MEASURER AAA

EVALUATION RESULT RELATED TO MOTOR FUNCTION OF SUBJECT 001 IS AS FOLLOWS

SUBJECT INFORMATION
……
```

EVALUATION RESULT ⬇

10 — DEMENTIA (SEVERE CASE) — 20 — DEMENTIA (MILD CASE) — MILD COGNITIVE IMPAIRMENT — NORMAL CONTROL — 30 → DEMENTIA SEVERITY SCORE MMSE

- ONE HAND METRONOME — NOT DONE
- BOTH HAND ALTERNATE FREE RUN — NOT DONE
- BOTH HAND SIMULTANEOUS FREE RUN — DONE
- ONE HAND FREE RUN — DONE

EVALUATION COMMENTS:
…….

[OVERLAY PAST RESULTS]    [END]

FIG. 19
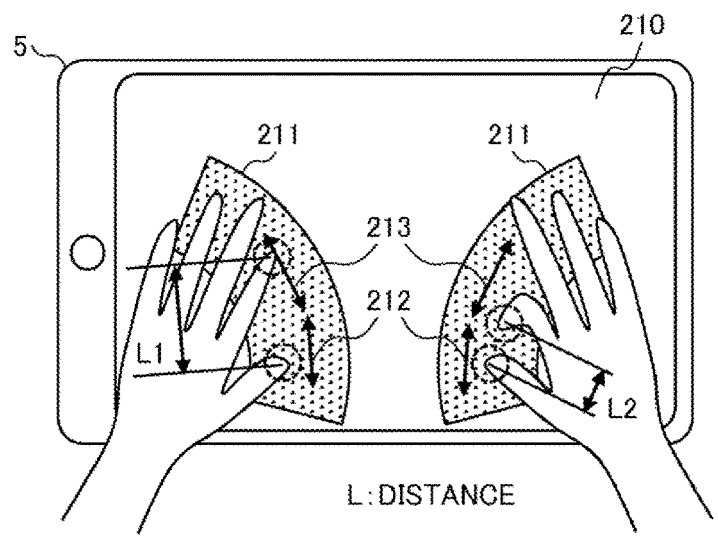
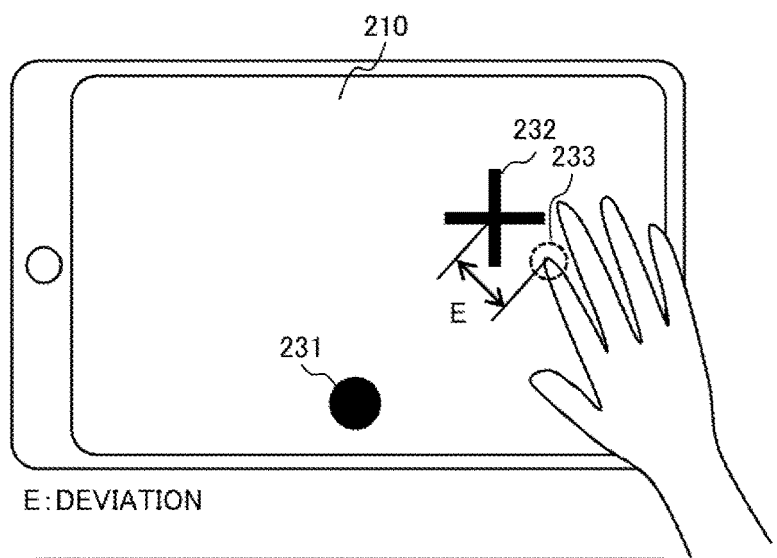
FIG. 20(A)
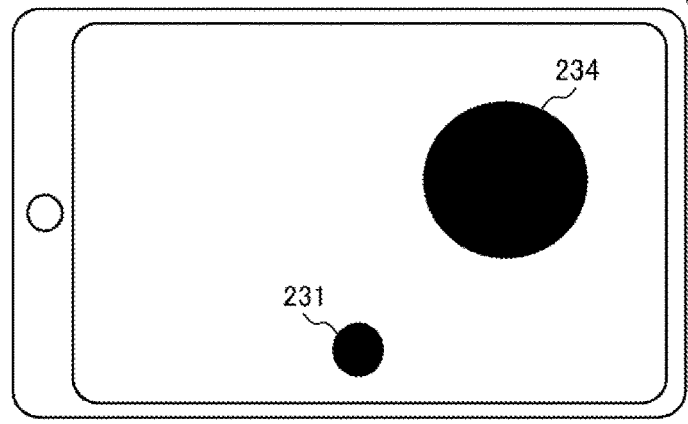
FIG. 20(B)

| SUBJECT ID | FACILITY ID | ON-SITE SUBJECT ID | GENDER | AGE | DISEASE | SEVERITY SCORE |
|---|---|---|---|---|---|---|
| 0001 | H001 | ****** | MALE | 55 | DEMENTIA | - |
| 0002 | H002 | A**** | FEMALE | 35 | NOT APPLICABLE (NORMAL CONTROL) | - |
| 0003 | H003 | X**** | ... | ... | ... | ... |
| ... | ... | ... | ... | ... | ... | ... |

| CONDITION | EYESIGHT | HEARING | HISTORY INFORMATION | ... |
|---|---|---|---|---|
| - | 1.0 | NO PARTICULAR | A11 {DATE AND TIME, TASK MEASUREMENT DATA, ANALYSIS EVALUATION DATA} A12 {DATE AND TIME, ······ } | ... |
| - | 0.8 | NO PARTICULAR | A21 {DATE AND TIME, ······ } | ... |
| ... | ... | ... | ... | ... |
| ... | ... | ... | ... | ... |

TASK EXECUTION ORDER DETERMINATION SYSTEM AND TASK EXECUTION METHOD

TECHNICAL FIELD

The present invention relates to information processing service technology. Further, the present invention relates to techniques for evaluating human cognitive and motor functions by a plurality of tasks of hand movements.

BACKGROUND ART

Systems or applications have been developed to easily evaluate the cognitive and motor functions of a person by measuring and analyzing the hand movements of the person. For example, a subject is asked to perform a task related to the movement of finger tapping (hereinafter may also referred to as "finger tap" or the like) with a sensor attached to the hand of the subject. Finger tapping is a movement of two fingers repeating opening and closing between contact state and separate state. There are various tasks in finger tapping. For example, finger tapping in one hand as quickly as possible with the largest amplitude possible is called one hand free run. Finger tapping in one hand opening and closing with a metronome is called one hand metronome. Finger tapping in left and right hands opening and closing at the same timing is called both hand simultaneous free run. Finger tapping in left and right hands opening and closing alternately is called both hand alternate free run.

A measurement device measures such finger tapping movement through a sensor. An evaluation device analyzes the nature and characteristic of the movement based on the measurement data, evaluates the cognition function and motor function of the person, and outputs results to a screen. The nature and characteristic of the movement can include, for example, number of finger taps, opening and closing distance, speed, and the like. For example, when the number of finger taps of a subject is smaller than the average of the number of finger taps of normal control subjects, the evaluation value of an index item such as momentum is reduced.

Further, the evaluation results obtained by the system can be used for the estimation of the subject's chance of disease, the evaluation of the severity of the disease, and the like. The disease includes movement disorders such as Parkinson's disease, in addition to various forms of dementia such as Alzheimer-type dementia, cerebrovascular dementia, and Lewy body dementia.

Japanese Patent No. 5330933 (Patent Literature 1) is cited as an example of prior art related to the hand movement measurement, analysis evaluation, disease estimation, and the like. Patent Literature 1 describes a method, as a motor function evaluation system, that performs processing such as generating a value representing the degree of motor impairment of a subject by comparing the characteristic quantity of finger tapping of the subject with the characteristic quantity of normal control subjects.

CITATION LIST

Patent Literature

PTL 1: Japanese Patent Application Laid-Open No. 2011-45520

SUMMARY OF INVENTION

Technical Problem

The conventional system has evaluated the cognitive function and the motor function by measuring only one type of task of hand movements. However, in order to evaluate such functions with a higher degree of accuracy, it is desirable to measure a plurality of types of hand movement tasks. However, when a subject or a measurer is asked to perform a plurality of hand movement tasks, the load on the subject or the measurer increases and this can cause the loss of the ease of testing. The load of the measurement becomes a more serious problem as the reduction in the subject's cognitive/motor function becomes more severe. For this reason, it is necessary to reduce the measurement load of hand movement tasks while maintaining the accuracy of evaluation.

In order to solve this problem, the present invention focuses on the fact that the range of severity of cognitive/motor function that can be accurately evaluated varies depending on the hand movement task. To cite the case of finger tapping, one hand free run can accurately evaluate a subject whose reduction in the cognitive/motor function is severe. On the other hand, both hands simultaneous free run can evaluate a moderate subject with a high degree of accuracy, and both hand alternate free run can accurately evaluate a mild subject with a high degree of accuracy. In other words, this means that the appropriate finger tapping task varies depending on the level of the cognitive/motor function of the subject. Based on this knowledge, it is necessary to measure the task appropriate for individual subject and not to measure unnecessary tasks.

Thus, an object of the present invention is to determine the execution order in which task measurement of hand movements is performed according to the level of reduction in the subject's cognitive/motor function, in order to achieve reduction in measuring the load on the subjects as well as improvement in accuracy of evaluation results at the same time.

Solution to Problem

An aspect of the present invention solving the above problems is a task execution order determination system that performs information processing to specify the execution order of a plurality of types of tasks. The task execution order determination system includes a processing device and a storage device. With respect to each of the plurality of types of tasks, the storage device stores a task ID identifying the task (or possibly other information, such as a task name, as long as the information can identify the task) as well as task execution order data for storing a parameter to determine the execution order of the task. The processing device specifies the execution order of the task based on the parameter. With respect to each of a plurality of measuring subjects, when a previously given score is associated with the discrimination index obtained from the execution result of the task, and when the plurality of measuring subjects are divided into two groups by a predetermined threshold of the score, the parameter is the predetermined threshold of score at which the discrimination accuracy for discriminating between the two groups by the discrimination index is maximized or above a given level.

An aspect of the present invention solving the above problems is a task execution order determination system that performs information processing to specify the execution order of a plurality of types of tasks. The task execution determination system includes a processing device and a storage device. With respect to each of the plurality of types of tasks, the storage device stores a task ID identifying the task (or possibly other information, such as a task name, as long as the information can specify the task), as well as task execution order data for storing a parameter to determine the execution order of the task. The processing device specifies the execution order of the task based on the parameter. With respect to each of a plurality of measuring subjects, when a previously given score and the discrimination index obtained from the execution result of the task, and when the plurality of measuring subjects are divided into two groups by a predetermined threshold of the score, the parameter is the predetermined threshold of score at which the discrimination accuracy for discriminating between the two groups by the discrimination index is minimized or below a given level.

An aspect of the present invention solving the above problems is a task execution method that determines the execution order of a plurality of tasks that a subject is asked to perform to obtain a characteristic quantity. This method is performed by an information processing device including a storage device and a processing device, using a subject group task database in which a previously given score and a characteristic quantity obtained by a plurality of tasks are stored as past data corresponding to each of the subjects. Based on the subject group task database, (1) a databased of discrimination accuracy when dividing the subjects into two groups by a predetermined threshold of the score and discriminating between the two groups by the characteristic quantity, or (2) a database of estimation accuracy when estimating the score by the characteristic quantity at the predetermined value of the score is prepared in the storage device for each of the tasks. The processing device performs: a first step of selecting the predetermined threshold of the score or the predetermined value of score at which the discrimination accuracy or the estimation accuracy is maximized or above a given level, as the optimal score, in each task, based on the database of discrimination accuracy or on the database of estimation accuracy; a second step of selecting a task from the plurality of tasks by referring to the optimal score and outputting information to perform the task; and a third step of obtaining results of the determination or results of the estimation by using the characteristic quantity obtained corresponding to the selected task.

Advantageous Effects of Invention

According to a typical embodiment of the present invention, it is possible to achieve both reduction in measuring the load on the subject as well as improvement in the accuracy of evaluation results, by determining and presenting the optimum execution order of a plurality of hand movement tasks for evaluating human cognitive and motor functions.

BRIEF DESCRIPTION OF DRAWINGS

FIG. 1 is a block diagram showing the configuration of a task execution order determination system according to a first embodiment of the present invention.

FIG. 7 is graph showing an example of wave signals of characteristic quantities in the first embodiment.

FIG. 8 is a schematic diagram showing a configuration example of characteristic quantity of a management table in the first embodiment.

FIG. 10A is graph showing the relationship between frequency distribution and characteristic quantity in the first embodiment.

FIG. 10C is a table showing an example of the evaluation accuracy database of one hand metronome in the first embodiment.

FIG. 10D is a table showing task execution order data in discrimination between two groups in the first embodiment.

FIG. 11B is a schematic diagram showing task execution order data in severity score estimation, according to the first embodiment.

FIG. 17 is a plan view showing an evaluation task screen (severity estimation) for measurement as an example of the display screen in the first embodiment.

FIG. 19 is a plan view showing finger tapping on the screen as a movement example in the second embodiment.

FIGS. 20(A) and 20(B) are plan views showing reaching as a movement example in the second embodiment.

FIG. 24 is a table showing a structure example of subject information, which is server management information, in the third embodiment.

DESCRIPTION OF EMBODIMENTS

Figure 2:
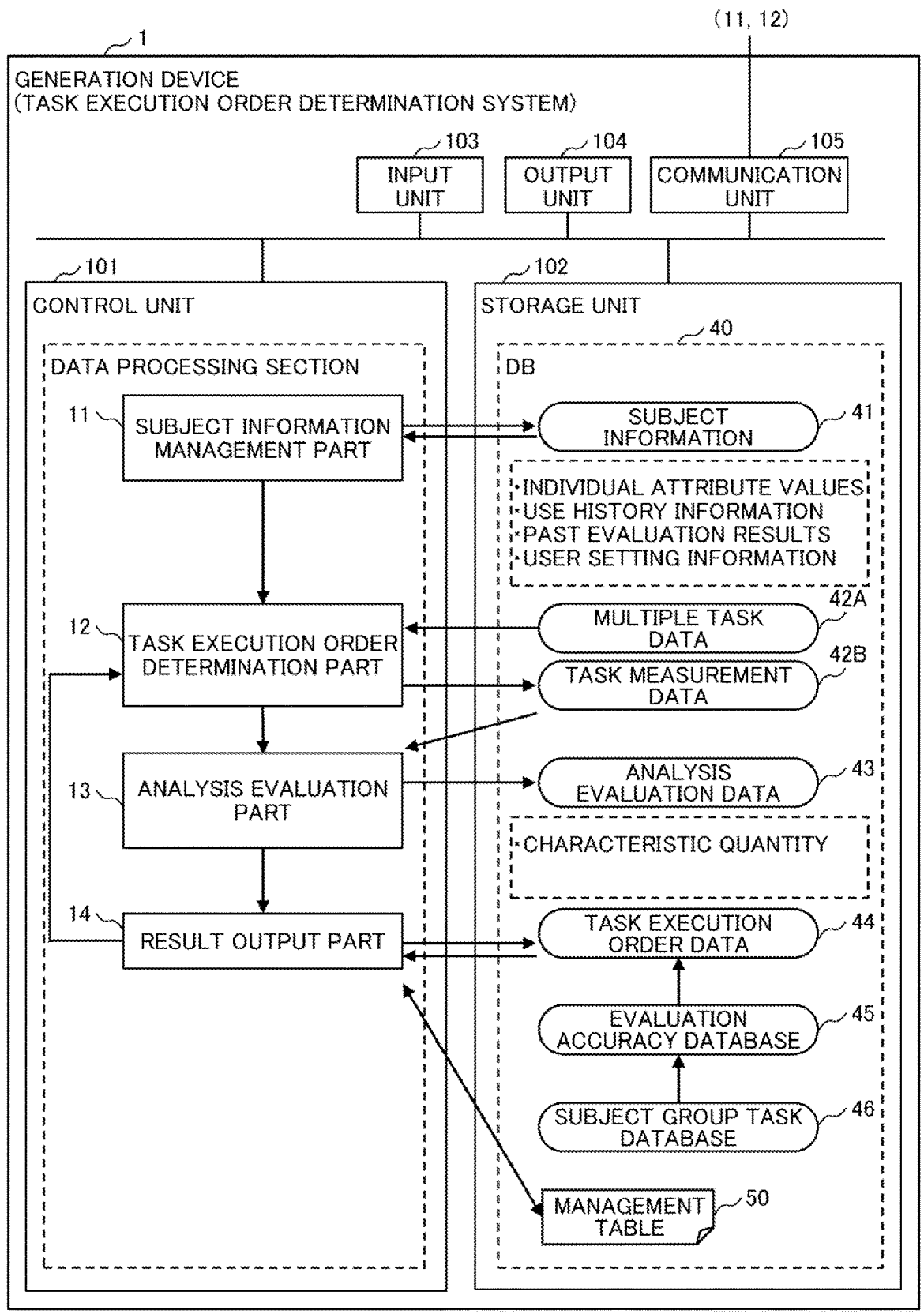
FIG. 2 is a functional block diagram showing the configuration of the task execution order determination system in the first embodiment.

As described above, according to the study of the present inventors, it is found that patients with different severities have different optimum tasks. From this finding, an example of the embodiments described in Examples is a task execution order determination system that performs information processing to determine the execution order of a plurality of tasks including human hand movement tasks. The task execution order determination system is characterized by having the following configuration.

In other words, a task execution order determination system according to an embodiment is a task execution order determination system that performs information processing to determine the execution order of hand movement tasks. The task execution order determination system includes: an evaluation accuracy database storage function for storing a database of discrimination accuracy of distribution of two groups obtained by dividing severity scores previously given to a subject group by a predetermined threshold, in a characteristic quantity calculated from the hand movement data of the subject group in a plurality of hand movement tasks, or a database of estimation accuracy of severity scores in a given range; an optimum severity score selection function for selecting the optimum severity score at which the discrimination accuracy or the estimation accuracy is maximized or above a given level in each task, from the database; a task execution function for selecting a task by referring to the optimum severity scores of the plurality of tasks and having the selected task performed; and a result presentation function for presenting the discrimination result or estimation result by using the characteristic quantity obtained by the selected task.

Hereinafter, embodiments of the present invention will be described in detail with reference to the accompanying drawings. Note that in all the drawings for describing the embodiments, the same components are basically denoted by the same reference numerals and the repetitive description thereof will be omitted. However, the present invention is not construed to be limited to the embodiments described below. Those skilled in the art can easily understand that specific configurations thereof can be modified without departing from the spirit or scope of the present invention.

The expressions such as "first", "second", and "third" used in this specification or other applicable documents are intended to identify the components and do not necessarily limit the number or order of components. Further, a number for identifying a component is used for each context and the number used in one context does not necessarily represent the same configuration in other contexts. In addition, the configuration identified by a certain number does not interfere with having the function of the component identified by a different number.

The position, size, shape, range, and the like of each configuration shown in the drawings or described herein may not represent the actual position, size, shape, range, and the like to facilitate the understanding of the present invention. Thus, the present invention is not necessarily limited to the position, size, shape, range, and the like disclosed in the drawings and the like.

Example 1

A task execution order determination system according to Example 1 (first embodiment) is described with reference to FIGS. 1 to 19. The task execution order determination system of the first embodiment generates an optimum order in which a plurality of hand movement tasks is performed in order to evaluate the cognitive function or motor function of a subject. The task execution order is the order in which previously given tasks are rearranged in the following order: the task good at evaluating subjects with severe reduction in motor function and cognitive function, the task good at evaluating moderate subjects, the task good at evaluating mild subjects, and so on.

In other words, the task execution order determination system presents evaluation results with a small number (one or two) of tasks to the subjects with severe reduction in motor function and cognitive function. On the other hand, the task execution order determination system displays evaluation results after measuring a large number of tasks to the subjects with mild reduction in motor function and cognitive function. In this way, the task execution order determination system of the first embodiment can achieve two advantages of accuracy improvement in evaluation results and reduction of measurement load on subjects, at the same time.

1-1. System (1)

FIG. 1 shows the configuration of a hand movement evaluation system including the task execution order determination system of the first embodiment. The first embodiment has a hand movement evaluation system on site. The hand movement evaluation system includes: a generation device 1 that configures the task execution order determination system; and an evaluation device 2 which is a finger tap movement evaluation device with magnetic sensors. The generation device 1 and the evaluation device 1 are connected through a communication line. The evaluation device 2 includes a measurement device 3 and a terminal device 4, which are connected through a communication line. A plurality of the evaluation devices 2 may be provided on site in the same manner.

The evaluation device 2 is a type of apparatus and system that measures hand movements by using a motion sensor with magnetic sensors. The motion sensor is connected to the measurement device 3. The motion sensor is attached to the hand of a subject. The measurement device 3 measures hand movements through the motion sensor and obtains measurement data including a time-series waveform signal.

The terminal device 4 displays various types of information on a display screen to support the evaluation of the cognitive/motor function of the subject by a measurer, and receives instruction input by the measurer. In the first embodiment, the terminal device 4 is a personal computer (PC).

The generation device 1 has a function as a service of information processing to determine the order of tasks of hand movement. The generation device 1 has, as its function, task measurement, analysis evaluation of cognitive/motor function or other factors, task execution order automatic generation, and the like.

The generation device 1 inputs, for example, instruction input, task measurement data, measurement data, and the like, as input data from the evaluation device 2. The generation device 1 outputs, for example, tasks, results, and the like, as output data to the evaluation device 2.

The task execution order determination system of the first embodiment can be widely applied to general facilities and people, without being limited to specific facilities, such as hospitals, as well as the subjects. The measurement device 3 and the terminal device 4 may be integrated into a single unit as the evaluation device 2. The terminal device 4 and the generation device 1 may be integrated into a single unit. The evaluation device 2 and the generation device 1 may be integrated into a single unit.

1-2. Task Execution Order Determination System

FIG. 2 shows the configuration of the generation device 1 according to the first embodiment. The generation device 1 includes a control unit 101, a storage unit 102, an input unit 103, an output unit 104, a communication unit 105, and the like, which are connected through a bus. For example, a computer such as a server can be used as hardware of the generation device 1. The input unit 103 is the part that performs instruction input by the administrator or other users of the generation device 1. The output unit 104 is the part that performs operations such as screen display to the administrator or other users. The communication unit 105 has a communication interface. The communication unit 105 is the part that performs communication processing with the measurement device 3 and the terminal device 4.

The control unit 101 controls the whole generation device 1. The control unit 101 is configured with CPU, ROM, RAM, and the like, to achieve a data processing section that performs task execution order determination processing or other operations based on software program processing. The data processing section of the control unit 101 includes a subject information management part 11, a task execution order determination part 12, an analysis evaluation part 13, and a result output part 14. The control unit 101 achieves functions such as a function for inputting measurement data from the measurement device 3, a function for processing and analyzing measurement data, a function for outputting control instructions to the measurement device 3 and the terminal device 4, and a function for outputting display data to the terminal device 4.

As described above, in this example, the functions such as calculation and control are achieved through a predetermined process in cooperation with other hardware devices in such a way that a software program stored in ROM, RAM, or the storage unit is executed by the CPU. Programs executed by a computer or the like, a function thereof, or means for achieving the function may be referred to as "function", "means", "part", "unit", "module", and the like. In this example, as a matter of convenience, each process may be described using these terms as subjects of sentences. Further, in this example, a function equivalent to the function configuring the software can also be achieved by hardware such as FPGA (Field Programmable Gate Array) or ASIC (Application Specific Integrated Circuit).

The subject information management part 11 performs a process of registering subject information input by the measurer into subject information 41 of a DB 40 and managing the registered subject information, a process of checking the subject information 41 of the DB 40 when the subject starts using the service, or other processes. The subject information 41 includes attribute value, use history information, subject setting information and the like for each individual subject. The attribute value includes gender, age, or other personal characteristics. The use history information is information that manages the history when the measurer uses the service that the system provides. The measurer setting information is setting information set by the measurer with respect to the function of the service.

The task execution order determination unit 12 is the part that performs a process of determining the execution order of tasks. The task execution order determination unit 12 outputs tasks on the screen of the terminal device 4 based on a plurality of task data 42A of the DB 40. Further, the task execution order determination unit 12 obtains task measurement data calculated by the measurement device 3, and then stores as task measurement data 42B in the DB 40.

The analysis evaluation part 13 is the part that performs analysis related to the cognitive and motor functions of a subject, as well as evaluation process based on the task measurement data 42B of the subject. The analysis evaluation part 13 performs processes such as extracting the nature and characteristic quantity of movement based on the task measurement data 42B, and calculating the evaluation value of a given index item such as motor function based on the characteristic quantity or other factors. The analysis evaluation part 13 stores analysis evaluation data 43, which is the result of the analysis evaluation process, into the DB 40.

Data or information stored in the DB 40 includes: subject information 41, task data 42A, task measurement data 42B, analysis evaluation data 43, task execution order data 44, evaluation accuracy database 45, subject group task database 46, management table 50, and the like. The control unit 101 maintains and manages the management table in the storage unit 102. The administrator can set the contents of the management table 50. Information such as characteristic quantity, index item, and type of task is set in the management table 50.

1-3. Measurement Device

Figure 3:
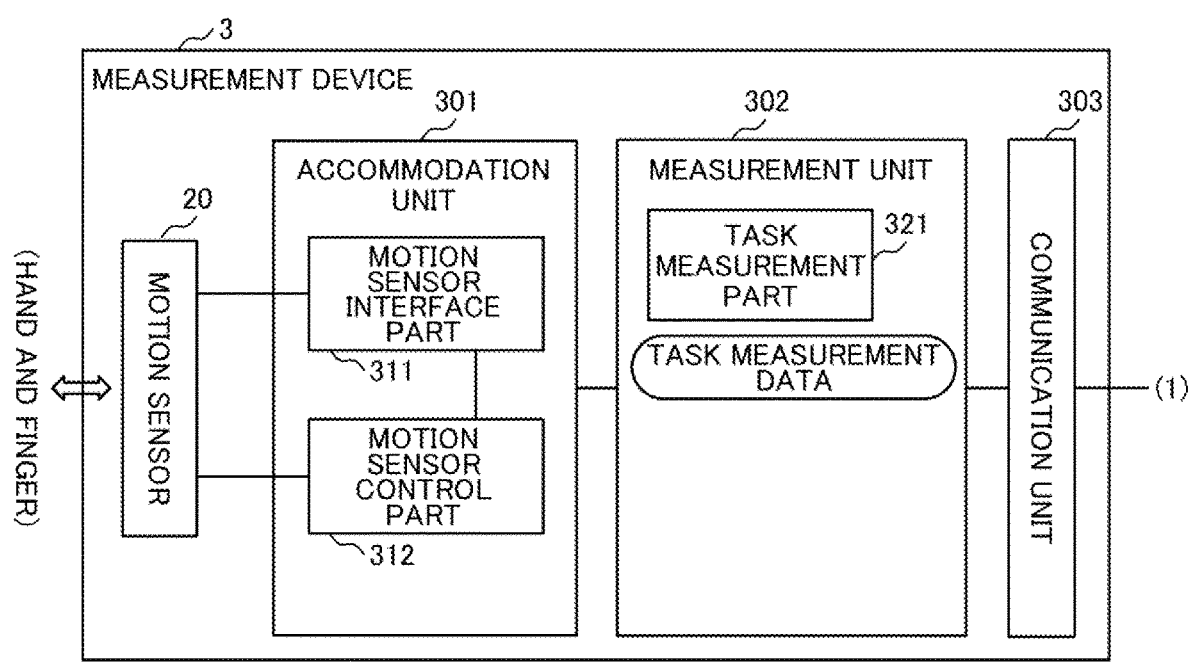
FIG. 3 is a block diagram showing the configuration of a measurement device in the first embodiment.

FIG. 3 shows the configuration of the measurement device 3 according to the first embodiment. The measurement device 3 includes a motion sensor 20, an accommodation unit 301, a measurement unit 302, a communication unit 303, and the like. The accommodation unit 301 includes a motion sensor interface part 311 to which the motion sensor 20 is connected, and a motion sensor control part 312 that controls the motion sensor 20. The measurement unit 302 measures a waveform signal through the motion sensor 20 and the accommodation unit 301, and outputs the waveform signal as measurement data. The measurement unit 302 includes a task measurement part 321 that obtains task measurement data. The communication unit 303 has a communication interface. The communication unit 303 communicates with the generation device 1 to transmit measurement data to the generation device 1. The motion sensor interface part 311 includes an analog/digital conversion circuit, converting an analog waveform signal detected by the motion sensor 20 into a digital waveform signal by sampling. The digital waveform signal is input to the motion sensor control part 312.

Note that the respective measurement data may be stored in storage means by the measurement device 3 or may be stored only in the generation device 1 without being stored in the measurement device 3.

1-4. Terminal Device

Figure 4:
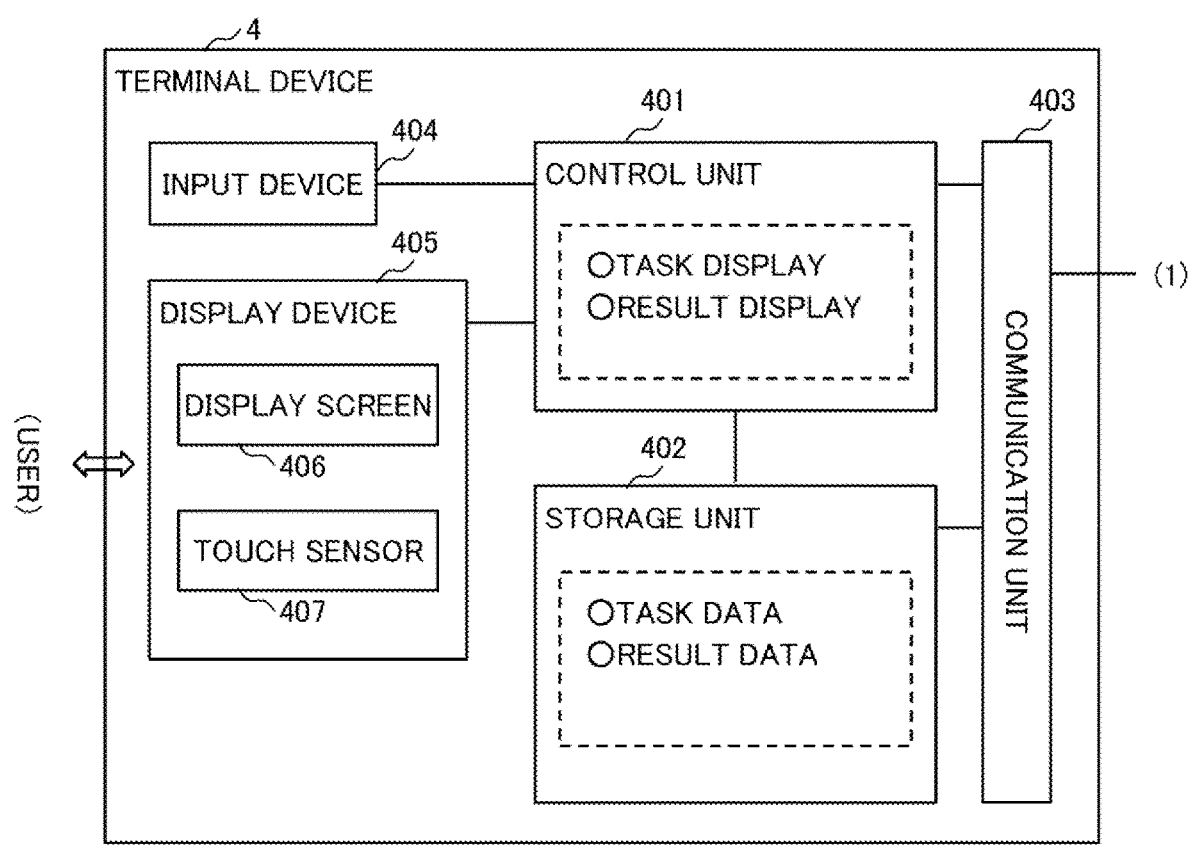
FIG. 4 is a block diagram showing the configuration of a terminal device in the first embodiment.

FIG. 4 shows the configuration of the terminal device 4 according to the first embodiment. The terminal device 4 is, for example, a PC and includes a control unit 401, a storage unit 402, a communication unit 403, an input device 404, and a display device 405. The control unit 401 receives task display, result display, measurer's instruction input, and the like, as control processes based on software program processing. The storage unit 402 stores task data, result data, and the like, obtained from the generation device 1. The communication unit 403 has a communication interface. The communication unit 403 communicates with the generation device 1 to receive various types of data from the generation device 1, and transmits the measurer's instruction input information or other information to the generation device 1. The input device 404 includes a keyboard, a mouse or other input devices. The display device 405 displays various types of information on a display screen 406. Note that a touch panel may be used as the display device 405.

1-5. Hand Movement Sensor, Finger Tapping Movement Measurement

Figure 5:
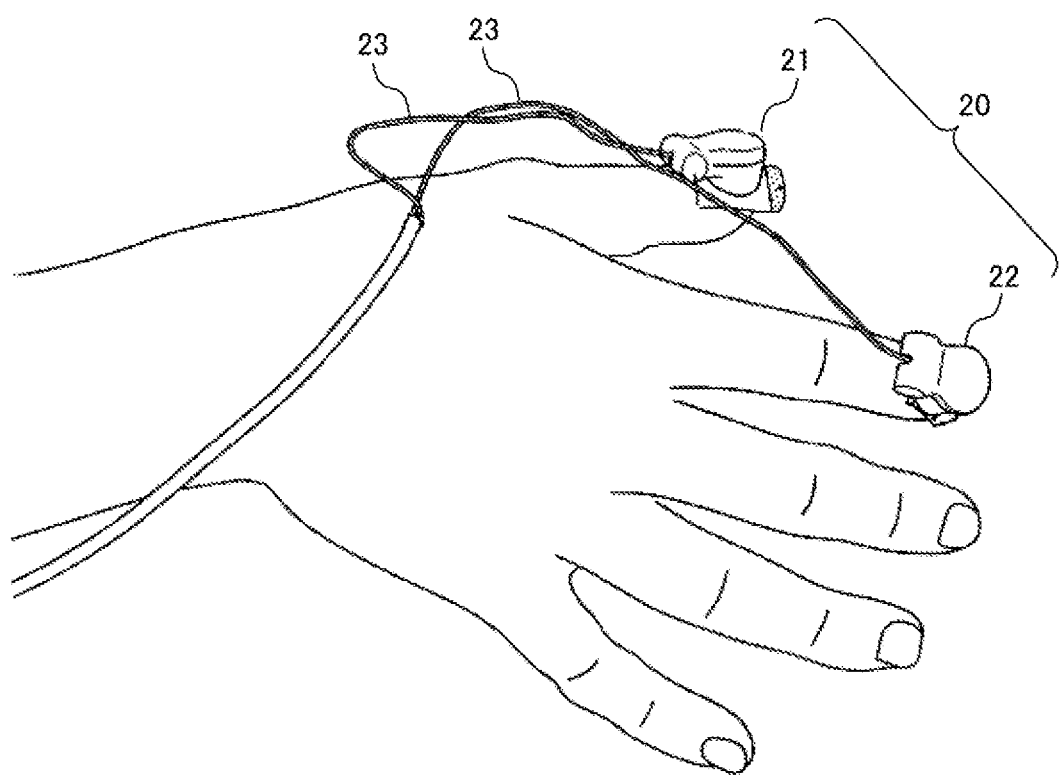
FIG. 5 is a perspective view showing a motion sensor attached to the hand in the first embodiment.

FIG. 5 shows the state in which a magnetic sensor, which is the motion sensor 20, is attached to the hand of a subject. The motion sensor 20 has a transmission coil unit 21 and a reception coil unit 22, which are a pair of coil units, through a signal line 23 connected to the measurement device 3. The transmission coil unit 21 generates a magnetic field and the reception coil unit 22 detects the magnetic field. In the example in FIG. 5, the transmission coil unit 21 is attached near the nail of the thumb and the reception coil unit 22 is attached near the nail of the index finger in the right hand of the subject. It is possible to change the finger to which the coil unit is attached. The part to which the coil units are attached is not limited to the vicinity of the nail. The coil units can be attached to other parts of finger.

As shown in FIG. 5, it is assumed that the motion sensor 20 is attached to the target hand of the subject, for example, two fingers of the thumb and index finger of the left hand. In this state, the subject performs finger tapping which is a movement of the two fingers repeating opening and closing. In the finger tapping, the subject performs the movement of transition between the state of the two fingers being closed, namely the state in which the ends of the two fingers contact each other, and the state of the two fingers being opened, namely the state in which the ends of the two fingers are opened. The distance between the coil units, the transmission coil unit 21 and the reception coil unit 22, which corresponds to the distance between the ends of the two fingers, changes due to this movement. The measurement device 3 measures a waveform signal corresponding to the change in the magnetic field between the transmission coil unit 21 and reception coil unit 22 of the motion sensor 20.

The finger tapping movement includes in more detail the following various types. The movement includes, for example, one hand free run, one hand metronome, both hand simultaneous free run, both hand alternate free run, both hand simultaneous metronome, both hand alternate metronome, and the like. One hand free run means performing finger tap several times with two fingers of one hand as quickly as possible. One hand metronome means performing finger tap with two fingers of one hand with a stimulus at a constant pace. Both hand simultaneous free run means performing finger tap with two fingers of the left hand and two fingers of the right hand at the same timing. Both hand alternate free run means performing finger tap with two fingers of the left hand as well as two fingers of the right hand at alternate timings. One hand free run and other finger tapping movements can be set as tasks.

1-6. Motion Sensor Control Unit and Finger Tapping Measurement

Figure 6:
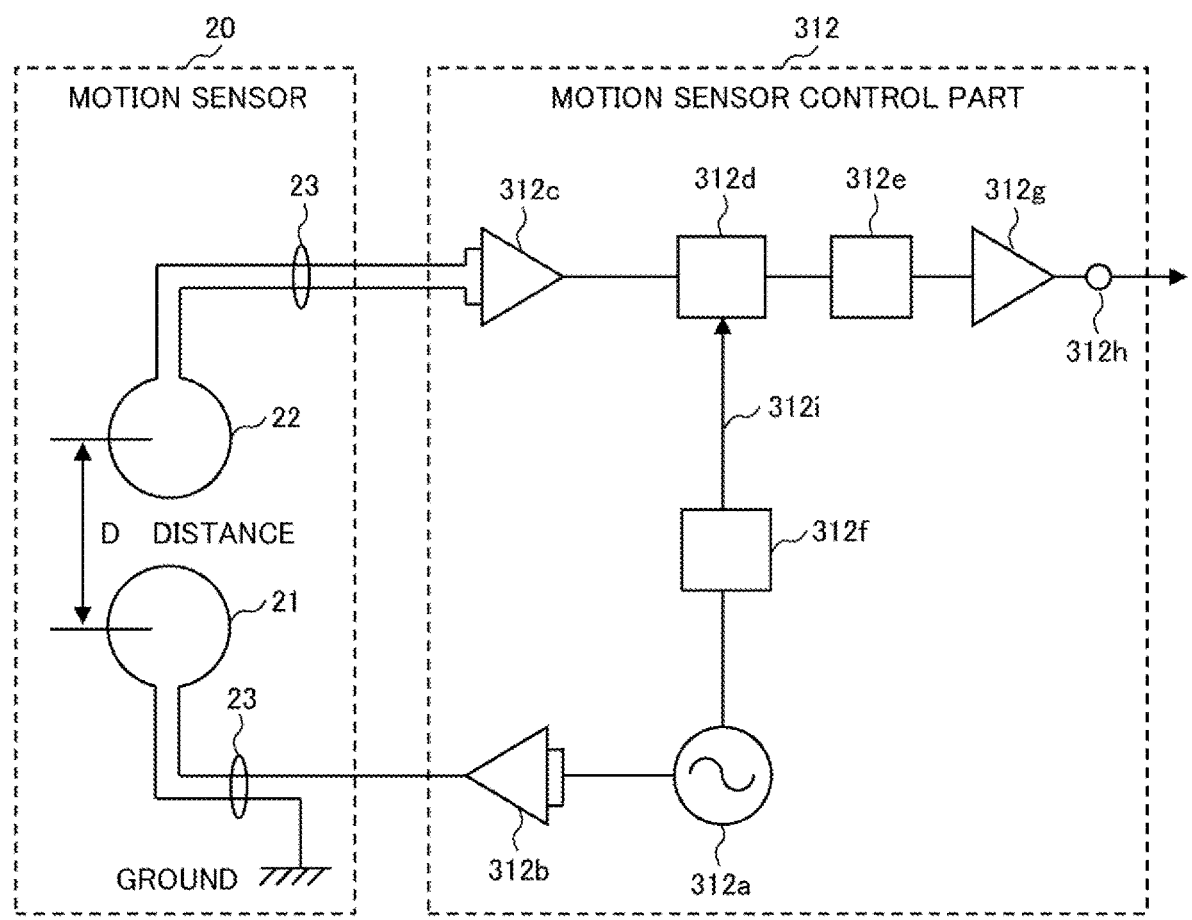
FIG. 6 is a block diagram showing the configuration of a motion sensor control unit and the like of the measurement device in the first embodiment.

FIG. 6 shows a detailed configuration example of the motion sensor control part 312 and other components of the measurement device 3. In the motion sensor 20, the distance between the transmission coil unit 21 and the reception coil unit 22 is represented by D. The motion sensor control part 312 includes an AC generation circuit 312a, a current generation amplifier circuit 312b, a preamplifier circuit 312c, a detection circuit 312d, an LPF circuit 312e, a phase adjustment circuit 312f, an amplifier circuit 312g, and an output signal terminal 312h. The current generation amplifier circuit 312b and the phase adjustment circuit 312f are connected to the AC generation circuit 312a. The transmission coil unit 21 is connected to the generation amplifier circuit 312b through the signal line 23. The reception coil unit 22 is connected to the preamplifier circuit 312c through the signal line 23. The detection circuit 312d, the LPF circuit 312e, the amplifier circuit 312g, and the output signal terminal 312h are connected in this order to the subsequent stage of the preamplifier circuit 312c. The detection circuit 312d is connected to the phase adjustment circuit 312f.

The AC generation circuit 312a generates an AC voltage signal of a predetermined frequency. The AC generation amplifier circuit 312b converts the AC voltage signal to an AC current of a predetermined frequency and outputs the result to the transmission coil unit 21. The transmission coil unit 21 generates a magnetic field by the AC current. The magnetic field causes the reception coil unit 22 to generate an induced electromotive force. The reception coil unit 22 outputs the AC current generated by the induced electromotive force. The AC current has the same frequency as the predetermined frequency of the AC voltage signal generated by the AC generation circuit 312a.

The preamplifier circuit 312c amplifies the detected AC current. The detection circuit 312d detects the amplified signal based on a reference signal 312i from the phase adjustment circuit 312f. The phase adjustment circuit 312f adjusts the phase of the AC voltage signal of a predetermined frequency or double frequency, and outputs the result as the reference signal 312i. The LPF circuit 312e outputs the detected signal with bandwidth constraint. The amplifier circuit 312g amplifies the signal to a predetermined voltage. Then, an output signal corresponding to the measured waveform signal is output from the output signal terminal 312h.

The waveform signal, which is the output signal, is a signal having a voltage value representing the distance D between the two fingers. The distance D and the voltage value can be converted based on a predetermined calculation formula. This formula can also be obtained by calibration. In calibration, for example, it is measured with the subject holding a block of a predetermined length with two fingers of the target hand. A predetermined calculation formula can be obtained from a data set of voltage value and distance value in the measured value, as an approximate curve that minimizes the error. Further, it is possible to know the size of the hand of the subject by calibration and use it to normalize the characteristic quantity. In the first embodiment, the magnetic sensor is used as the motion sensor 20, and the measurement means corresponding to the magnetic sensor is used. However, the present invention is not limited to this example. Other detection means and measurement means, such as acceleration sensor, stain gauge, and high-speed camera, can also be applied.

1-7. Characteristic Quantity

FIG. 7 shows an example of the waveform signal of the characteristic quantity. In FIG. 7, (a) shows the waveform signal of the distance D between the two fingers, (b) shows the waveform signal of the speed of the two fingers, and (c) shows the waveform signal of the acceleration of the two fingers. The speed in (b) can be obtained by temporal differentiation of the waveform signal of the distance in (a).

The analysis evaluation part 13 obtains a waveform signal of a predetermined characteristic quantity like this example from the waveform signal of the task measurement data 42B, based on calculations such as differentiation and integration. Further, the analysis evaluation part 13 obtains a value from the characteristic quantity by a predetermined calculation.

FIG. 7 (d) is an enlarged view of (a), showing an example of the characteristic quantity. The figure shows the maximum value Dmax of the distance D in finger tap, the tap interval TI, and the like. The vertical dashed line represents the average Dav of the distance D in the total measurement time. The maximum value Dmax represents the maximum value of the distance D in the total measurement time. The tap interval TI is the time corresponding to the cycle TC of one finger tap, particularly showing the time from a minimum point Pmin to the next minimum point Pmin. In addition, the maximum point Pmax and the minimum point Pmin in one cycle of the distance D, as well as the time T1 of the opening movement and the time T2 of the closing movement, which are described below.

A further detailed example of the characteristic quantity is shown below. The first embodiment uses a plurality of characteristic quantities including the distance, the speed, the acceleration, as well as characteristic quantity parameter values described below. Note that in other embodiments, only some of the characteristic quantities may be used, or other characteristic quantities may be used. The details of the definition of the characteristic quantity are not particularly limited.

FIG. 8 shows the part of the characteristic quantity [distance] of the setting information of the association between the characteristic quantity and the index item in the management table 50. This association setting is an example and can be changed. The management table 50 in FIG. 8 has, as columns, characteristic quantity classification, identification number, characteristic quantity parameter, and index item. The characteristic quantity classification includes [distance], [speed], [acceleration], [tap interval], [phase difference], and [marker tracking]. For example, the characteristic quantity [distance] has a plurality of characteristic quantity parameters identified by identification numbers (1) to (7). Values in parentheses of the characteristic quantity parameters represent units. Each parameter is associated with a predetermined index item.

(1) "Maximum amplitude of distance" [mm] is the difference in amplitude between the maximum value and the minimum value in the distance waveform ((a) in FIG. 7). The parameters of (1), (4), (6), and (7) are associated with the index item F (tracking ability) and the index item H (amplitude control). (2) "Total movement distance" [mm] is the sum of the absolute values of the distance change in the total measurement time of one measurement. This parameter is associated with the index item A (momentum). (3) "Average of maximum point of distance" [mm] is the average of the values of the maximum point of the amplitude in each cycle. This parameter is associated with the index item F (tracking ability). (4) "Standard deviation of maximum point of distance" [mm] is the standard deviation related to the above value.

(5) "Slope of approximate curve of maximum point of distance (decay rate)" [mm/sec] is the slope of a curve that approximates maximum points of the amplitude. This parameter represents the amplitude change mainly due to fatigue during the measurement time. This parameter is associated with the index item B (endurance). (6) "Coefficient of variation of maximum point of distance" is the coefficient of variation of the maximum point of the amplitude, and its unit is a dimensionless quantity (indicated by "[-]"). This parameter is the value obtained by normalizing the standard deviation by the average, and thus the individual variation in finger length can be eliminated. (7) "Standard deviation of local maximum point of distance" [mm] is the standard deviation of maximum points of the amplitude at three adjacent positions. This parameter is the parameter for evaluating the degree of local amplitude variation in a short amount of time.

Hereinafter, although not shown in the figure, each of the characteristic quantity parameters will be described. With respect to the characteristic quantity [speed], the management table 50 has the following characteristic quantity parameters indicated by identification numbers (8) to (22). (8) "Maximum amplitude of speed" [m/sec] is the difference between the maximum value and the minimum value in the speed waveform ((b) in FIG. 7). The parameters (8) to (10) are associated with the index item F. (9) "Average of maximum point of opening speed" [m/sec] is the average with respect to the maximum value of the speed of the opening movement of each finger tap waveform. The opening movement is the movement of changing the state of two fingers from a closed state to a maximum open state ((d) in FIG. 7). (10) "Average of maximum point of closing speed" [m/sec] is the average with respect to the maximum value of the speed in closing movement. The closing movement is the movement of changing the state of two fingers from the maximum open state to the closed state. (11) "Standard deviation of maximum point of opening speed" [m/sec] is the standard deviation with respect to the maximum value of the speed in the opening movement. (12) "Average of maximum point of closing speed" [m/sec] is the standard deviation with respect to the maximum value of the speed in the closing movement. The parameters of (11), (12), (15), and (16) are associated with the index item F and the index item H.

(13) "Energy balance" [-] is the ratio of the sum of squares of the speed during the opening movement to the sum of squares of the speed during the closing movement. The parameters of (13) and (17) to (22) are associated with the index item G. (14) "Total energy" [$m^2/sec^2$] is the sum of squares of the speed in the total measurement time. This parameter is associated with the index item A. (15) "Coefficient of variation of maximum point of opening speed" [-] is the coefficient of variation with respect to the maximum value of the speed in the opening movement, which is the value obtained by normalizing the standard deviation by the average. (16) "Average of maximum point of closing speed" [m/sec] is the coefficient of variation with respect to the maximum value of the speed in the closing movement.

(17) "Number of involuntary movements" [-] is the number obtained by subtracting the number of large opening and closing movements in finger tap from the number of times that the positive and negative peaks of the speed waveform change. (18) "Average of distance ratio at peak of opening speed" [-] is the average for the ratio when the finger tap amplitude is 1.0, with respect to the distance when the speed is maximum during the opening movement. (19) "Average of distance ratio at peak of closing speed" [-] is similarly the average for the ratio, with respect to the distance when the speed is maximum during the closing movement. (20) "Proportion of distance ratio at peak speed" [-] is the proportion between the value of (18) and the value of (19). (21) "Standard deviation of distance ratio at peak opening speed" [-] is the standard deviation for the ratio when the finger tap amplitude is 1.0, with respect to the distance when the speed is maximum during the opening movement. (22) "Standard deviation of distance ratio at peak closing speed" [–] is similarly the standard deviation for the ratio with respect to the distance when the speed is minimum during the closing movement.

With respect to the characteristic quantity [acceleration], the management table 50 has the following characteristic quantity parameters indicated by identification numbers (23) to (32). (23) "Maximum amplitude of acceleration" [m/sec$^2$] is the difference between the maximum value and minimum value of the acceleration in the acceleration waveform ((c) in FIG. 7). The parameters (23) to (27) are associated with the index item F. (24) "Average of maximum point of opening acceleration" [m/sec$^2$] is the average of the maximum value of the acceleration during the opening movement, which is the first value of four types of extreme values appearing in one cycle of finger tap movement. (25) "Average of minimum point of opening acceleration" [m/sec$^2$] is the average of the minimum value of the acceleration in the opening movement, which is the second value of the four types of extreme values. (26) "Average of maximum point of closing accelerations" [m/sec$^2$] is the average of the maximum value of the acceleration in the closing movement, which is the third value of the four types of extreme values. (27) "Average of minimum point of closing acceleration" [m/sec$^2$] is the average of the minimum value of the acceleration in the closing movement, which is the fourth value of the four types of extreme values.

(28) "Average of contact time" [sec] is the average of the contact time in the closed state of two fingers. The parameters (28) to (32) are associated with the index item G. (29) "Standard deviation of contact time" [sec] is the standard deviation of the contact time. (30) "Coefficient of variation of contact time" [–] is the coefficient of variation of the contact time. (31) "Number of acceleration zero crossings" [–] is the average number of times that the positive and negative peaks of the acceleration change in one cycle of finger tap. This value is ideally two. (32) "Number of freezing events" [–] is the value obtained by subtracting the number of large opening and closing movements in finger tap from the number of times that the positive and negative peaks of the acceleration change in one cycle of finger tap.

With respect to the characteristic quantity [tap interval], the management table 50 has the following characteristic quantity parameters indicated by identification numbers (33) to (41). (33) "Number of taps" [–] is the number of finger taps in the total measurement time of one measurement. The parameters (33) to (35) are associated with the index item A. (34) "Tap interval average" [sec] is the average with respect to the tap interval in the distance waveform ((d) in FIG. 7). (35) "Tap frequency" [Hz] is the frequency at which the spectral is maximum when the distance waveform is Fourier-transformed. (36) "Tap interval standard deviation" [sec] is the standard deviation with respect to the tap interval. The parameters (36) to (40) are associated with the index item C and the index item I.

(37) "Coefficient of variation of tap interval" [–] is the coefficient of variation with respect to the tap interval, which is the value obtained by normalizing the standard deviation by the average. (38) "Variation in tap interval" [mm$^2$] is the integrated value with a frequency of 0.2 to 2.0 Hz, when the tap interval is spectrally analyzed. (39) "Skewness of tap interval distribution" [—] is the skewness in the frequency distribution of the tap interval, which represents the degree to which the frequency distribution is distorted as compared to the normal distribution. (40) "Standard deviation of local tap interval" [sec] is the standard deviation with respect to the tap interval of adjacent three positions. (41) "Slope of approximate curve of tap interval (decay rate)" [–] is the slope of the curve that approximates the tap interval. This slope mainly represents the change in the tap interval due to fatigue during the measurement time. This parameter is associated with the index item B.

With respect to the characteristic quantity [phase difference], the management table 50 has the following characteristic quantity parameters indicated by identification numbers (42) to (45). (42) "Average of phase difference" [degree] is the average of the phase difference between the waveforms of both hands. The phase difference is an index value that represents the deviation of the left hand finger tap from the right hand, in which one cycle of the right hand finger tap is 360 degrees. It is assumed that the index value is 0 degrees when there is no deviation in the phase. The deviation between the two hands increases as the values of (42) and (43) become larger, which indicates instability. The parameters (42) to (45) are associated with the index item D and the index item J. (43) "Standard deviation of phase difference" [degree] is the standard deviation with respect to the phase difference. (44) "Similarity between both hands" [–] is the value representing the correlation when the time lag 0, when the cross-correlation function is applied to the waveforms of the left and right hands. (45) "Time lag maximizing similarity between both hands" [sec] is the value representing the time lag that maximizes the correlation (44).

With respect to the characteristic quantity [marker tracking], the management table 50 has the following characteristic quantity parameters indicated by identification numbers (46) to (47). (46) "Average of delay time from marker" [sec] is the average with respect to the finger tap delay time from the time indicated by a cyclical marker. The marker corresponds to a stimulus such as visual stimulation, auditory stimulation, or tactile stimulation. This parameter value is based on the time point at which the two fingers are closed. The parameters (46) and (47) are associated with the index item E. (47) "Standard deviation of delay time from marker" [sec] is the standard deviation with respect to the delay time.

1-8. Process Flow

Figure 9:
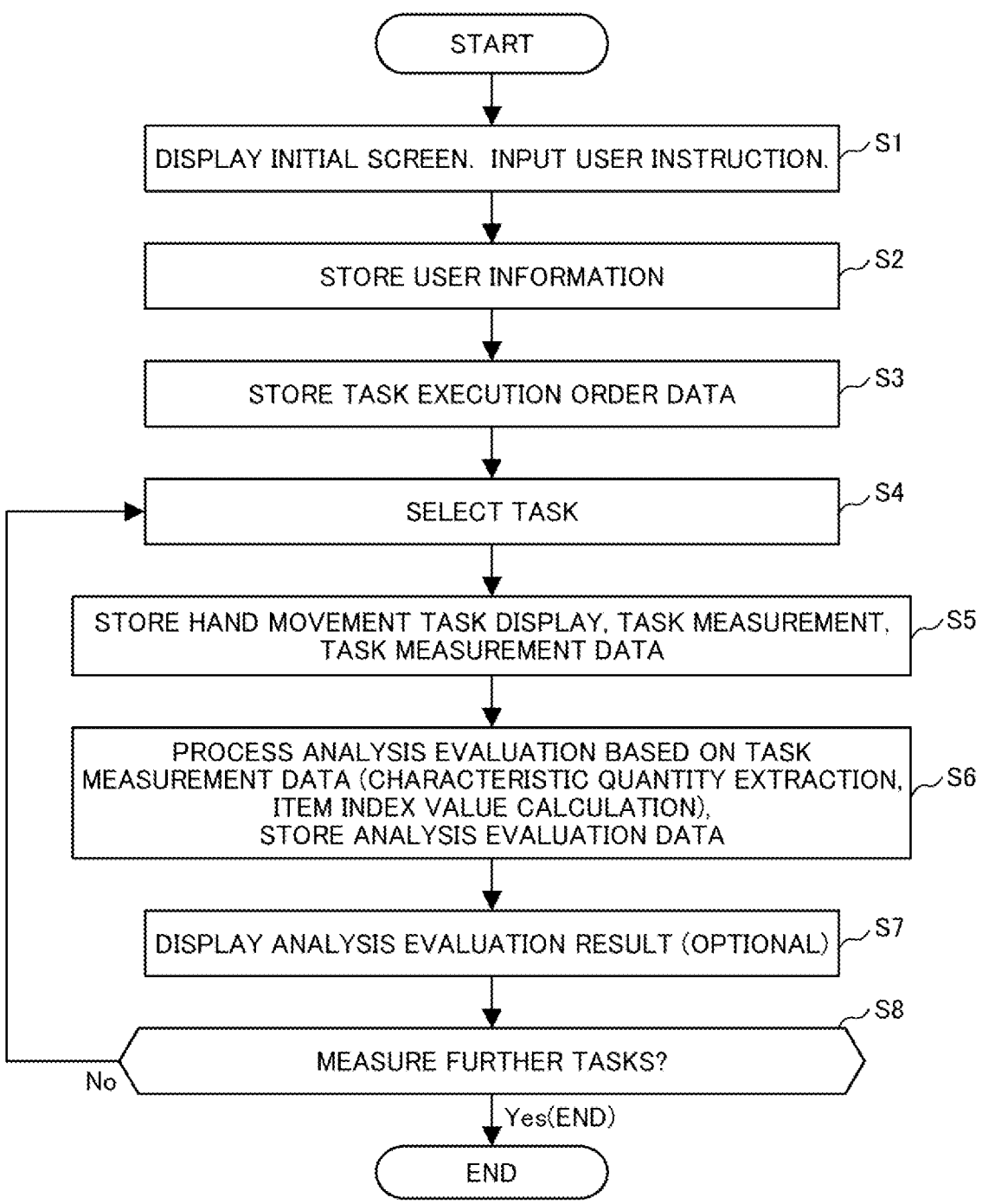
FIG. 9 is a flowchart showing the process flow of the task execution order determination system of the first embodiment.

FIG. 9 shows the flow of the whole process mainly performed by the generation device 1 and the evaluation device 2 in the task execution order determination system of the first embodiment. FIG. 7 has Steps S1 to S8. The steps will be described sequentially below.

(S1) The measurer operates the evaluation device 2. The terminal device 4 displays an initial screen on the display screen. The measurer selects a desired operation item on the initial screen. For example, the operation item to perform an evaluation of hand movement is selected. The terminal device 4 transmits instruction input information corresponding to the selection to the generation device 1. Further, the measurer can also input and register subject information such as gender and age on the initial screen. In this case, the terminal device 4 transmits the input subject information to the generation device 1. The subject information management part 11 of the generation device 1 registers the subject information in the subject information 41.

(S2) The measurer inputs personal information, such as the age, gender, and past diagnosis information of the subject, from the input device 404.

(S3) The task execution order determination part 12 reads the task execution order data 44 that shows the execution order of hand movement tasks and stores the read data in the DB 40. The determination method of the task execution order data 44 will be described below. The task execution order data 44 is calculated from the evaluation accuracy database 45, and the evaluation accuracy database 45 is calculated from the subject group task database 46. The evaluation accuracy database 45 and the task execution order data 44 are updated each time the subject group task database 46 is updated.

(S4) The measurer selects a task that the subject is asked to perform, from the task execution order data 44. At this time, the subject's personal information obtained in S2 or the past hand task evaluation result stored in the DB 40 can be used for the selection. The task selection method will be described below.

(S5) The task execution order determination part 12 of the generation device 1 transmits the task data for the subject to the terminal device 4 based on the instruction input information in S1 as well as the task data 42A. The task data includes information of one or more types of tasks related to hand movement. The terminal device 4 displays the task information of hand movement on the display screen based on the received task data. The subject performs the task of hand movement according to the task information on the display screen. The measurement device 3 measures the task, and transmits the result as task measurement data to the generation device 1. The generation device 1 stores the task measurement data in the task measurement data 42B.

(S6) The analysis evaluation part 13 of the generation device 1 performs the analysis evaluation process of the subject's motor function or the like. Then, the analysis evaluation part 13 generates the analysis evaluation data 43 of the subject and stores in the DB 40. In the analysis evaluation process, the analysis evaluation part 13 extracts a characteristic quantity based on the waveform signal of the task measurement data 42B of the subject. The characteristic quantity includes distance, speed and the like described below. The analysis evaluation part 13 calculates an evaluation value of an index item representing motor function or the like. The index item includes momentum, endurance and the like described below. For example, the analysis evaluation part 13 calculates an evaluation value for each index item by a predetermined calculation that integrates characteristic quantities to be associated with the index item. There is no limitation on the method of this calculation.

Note that as a simple evaluation method, it is possible to directly use a predetermined characteristic quantity as the evaluation value. Further, the analysis evaluation part 13 may correct the extracted characteristic quantity based on the attribute value such as the age of the subject. Then, the analysis evaluation part 13 may use the corrected characteristic quantity for the evaluation.

(S7) The result output part 16 of the generation device 1 outputs the analysis evaluation result information on the display screen of the terminal device 4 based on the analysis evaluation result data 43 in S3. The measurer and the subject can check the analysis evaluation result information that shows the state of the subject's own motor function or the like on the display screen. Step 4 can be omitted from the flow. The result display method will be described below.

(S8) When wanting to obtain evaluation results with a high degree of accuracy by measuring still more number of hand movement tasks, the measurer selects an operation item to perform evaluation on the display screen of the terminal device 4. The terminal device 4 transmits the instruction input information corresponding to the selection, to the generation device 1. It may also be possible to omit Step S5 and automatically proceed to the process of measuring the next hand movement task. When the measurer does not measure the next hand movement task in S5, the flow ends.

1-9. Determination Method of Task Execution Order Data

When a plurality of tasks are given in advance, the generation device 1 obtains a range of severity with which two-group discrimination or severity estimation can be performed accurately in each task. This process requires a database of measurement data of a large number of subjects in each task.

<1-9-1. Case of Two-Group Discrimination>

The case of performing two-group discrimination by task will be described. It is assumed that the following four types of tasks are given in advance: one hand free run, one hand metronome, both hand simultaneous free run, and both hand alternate free run. A database of measuring each of the tasks for a large number of subject groups is prepared and the database is stored in the subject group task database 46. At this time, a score of evaluation of cognitive/motor function in the same subject group is also obtained in advance. This score may be a score visually evaluated by a health care professional such as doctor, occupational therapist, or physical therapist, or a score obtained by other testing equipment. Such a score is also referred to as severity score. In this example, the generation device 1 uses the score of Mini-Mental State Examination (hereinafter, MMSE) in which a doctor visually evaluates the cognitive function.

The score of MMSE is an integer in the range of 0 to 30 points. As a guide, it is said that MMSE with 28 points or more corresponds to normal control, 24 to 27 points corresponds to mild cognitive impairment between cognitive impairment and normal control, and 23 points or less corresponds to cognitive impairment. In this way, the scores of MMSE, as well as the measurement results and characteristic quantities obtained by a plurality of types of tasks are stored in the subject group task database 46 for each subject.

Now consider the case of discriminating a group of subject into two groups, a group of less than N points and a group of above N points, by using finger tapping data, assuming that each point of integers is a threshold N in increments of one point of MMSE. In other words, it is possible to discriminate a group of subjects into two groups by the threshold N of MMSE with the scores of MMSE given by professionals as reference, and consideration is given to automatically performing the discrimination by using a characteristic quantity p of finger tapping described above with a high degree of accuracy. It is possible to determine p by selecting one characteristic quantity, as a discrimination index, from 47 characteristic quantities, or by calculating one discrimination index from a plurality of characteristic quantities by using statistical methods such as main component analysis, multiple regression analysis, and discriminant analysis. In this example, one discrimination index is calculated from a plurality of characteristic quantities by using multiple regression analysis based on the stepwise variable selection method. The accuracy in discriminating between the two groups is evaluated by Area Under ROC Curve (AUC). AUC is values between 0 and 1, showing that the closer the value is to 1 the higher the discrimination accuracy. It may also be possible to evaluate the discrimination accuracy by indices other than AUC, such as sensitivity, specificity, and correct discrimination ratio.

As shown in FIG. 10A (a) and (b), the generation device 1 discriminates between the two groups of less than N points and of above N points based on the discrimination index (or the characteristic quantity p), by changing the threshold of MMSE in increments of one point. FIG. 10A (a) and (b) show data of one task, in which the horizontal axis represents the characteristic quantity and the vertical axis represents the frequency distribution of data with respect to the characteristic quantity, for example, the number of samples of subjects. As an example, assuming MMSE threshold N=27 points, FIG. 10A (a) shows discrimination between a group of less than 27 points of MMSE and a group of above 27 points of MMSE. In other words, FIG. 10A (a) conceptually shows the group of less than MMSE 27 points and the group of above MMSE 27 points, as different distribution curves. Similarly, assuming MMSE threshold N=20, FIG. 10A (b) shows discrimination between a group of less than MMSE 20 points and a group of above MMSE 20 points.

In this way, if the threshold N varies, the manner of discrimination between the two groups may vary and the discrimination accuracy (AUC) may vary even if the characteristic quantity is the same. The discrimination accuracy is increased when the two groups are clearly discriminated, while the discrimination accuracy is reduced when the overlapping part of the two groups is large. In FIG. 10A (a), the discrimination accuracy AUC is 0.9. In FIG. 10A (b), the discrimination accuracy AUC is 0.6. This shows that when the characteristic quantity p of the task is used, the accuracy is higher in the process of discriminating the subject group into two groups by MMSE 27 than in the process of discriminating the subject group into two groups by MMSE 20.

Figure 10B:
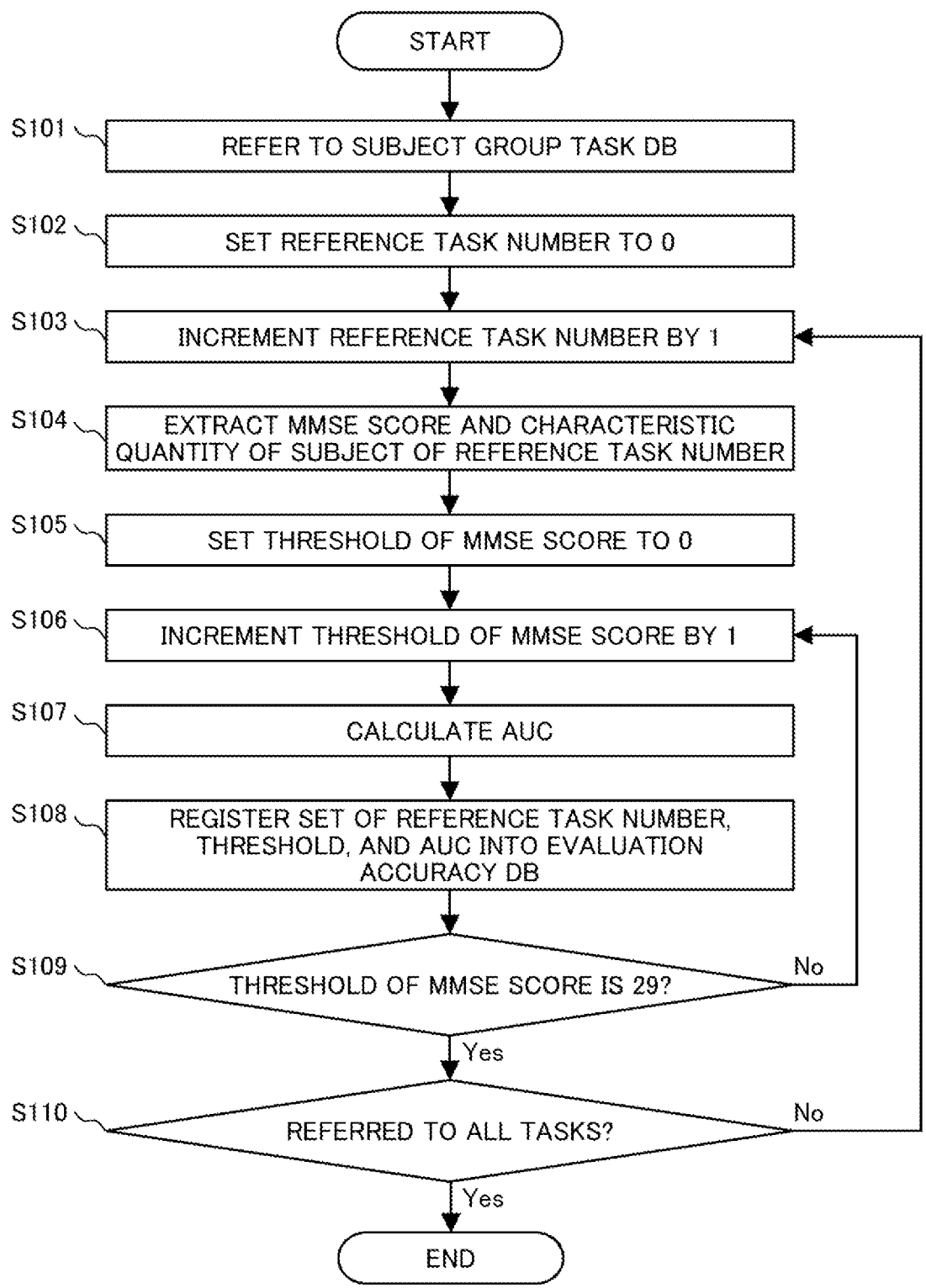
FIG. 10B is a flowchart showing the flow of the process of generating an evaluation accuracy database from a subject group datable.

Referring to FIG. 10B, the following describes an example of the process of generating the evaluation accuracy database 45 by calculating the discrimination accuracy AUC by shifting the threshold N point in increments of one point as described above.

In step S101, the generation device 1 refers to the subject group task database 46.

In step S102, of the data of a plurality of types of tasks stored in the subject group task database 46, the generation device 1 sets the task number (reference task number) of the task, which should be referred to in the process, to zero. In this example, it is assumed that task numbers (IDs) for identifying tasks are stored in the subject group task database 46 in integers of 1 or more in ascending order.

In step S103, the generation device 1 increments the reference task number by one.

In step S104, the generation device 1 extracts the MMSE score and characteristic quantity of a subject, with respect to the task identified by the reference task number. When the extracted data is used, as shown in FIG. 10A, it is possible to obtain the appearance frequency distribution of the subject for the characteristic quantity p, with respect to a certain task.

In step S105, the generation device 1 sets the threshold of the MMSE score to 0.

In step S106, the generation device 1 increments the threshold of the MMSE score by 1.

In step S107, with respect to the particular task, the generation device 1 divides the subject appearance frequency distribution into two groups by using the threshold of the MMSE score determined in step S106. Then, the generation device 1 calculates the discrimination accuracy AUC in the case of discriminating between the two groups by using the threshold of the characteristic quantity p. The concept of this process is as described in FIG. 10A. Note that the threshold of the characteristic quantity p (or discrimination index) will be described below.

In step S108, the generation device 1 registers data of a combination of reference task number (or task name or ID), MMSE score threshold, and AUC into the evaluation accuracy database 45.

In step S109, the generation device 1 determines whether the threshold of the MMSE score is 29. If the threshold is less than 29, the process returns to step S106. Because only the range of values from 1 to 29 is meaningful as a two-division threshold, the generation device 1 changes the threshold N of the MMSE score in increments of one point in the range of 1 to 29 points, and calculates the discrimination accuracy AUC at each threshold. When the threshold of the MMSE score is 29, all thresholds are applied for the particular task, and thus the process proceeds to step S110.

In step S110, the generation device 1 checks whether the process is completed on all tasks. If not completed, the generation device 1 returns to step S103 and performs the process on the next task. When completed, the generation or update of the evaluation accuracy database 45 is completed, and the process ends.

By the process described above, the threshold of the MMSE score and the data of AUC corresponding to the threshold are stored in the evaluation accuracy database 45 in each task. Thus, it is possible to obtain a threshold Nmax of the MMSE score that maximizes AUC from the stored data, in each task. The larger the number of subjects, the more the content is expected to be relevant to the evaluation accuracy database 45. Thus, it is desirable that the evaluation accuracy database 45 is updated according to the update of the subject group task database 46.

FIG. 10C is a portion of the evaluation accuracy database 45 obtained by the process in FIG. 10B, which is data showing the evaluation accuracy of one hand metronome. In addition to this, data of other tasks are also stored in the evaluation accuracy database 45 but the structure is the same and omitted here.

In the evaluation accuracy database 45, with respect to the threshold N of the MMSE score, thresholds $Y_{th1}$ to $Y_{th29}$ of the discrimination index for discriminating between two groups divided by the threshold N are stored. As shown in FIG. 10A, with respect to the thresholds $Y_{th1}$ to $Y_{th29}$, it is assumed that thresholds for discriminating between two groups by the discrimination index (or characteristic quantity p) are determined in advance by a general method. For example, as shown in FIG. 10A (c), there is a method of drawing a Receiver Operatorating Characteristic curve (hereinafter, ROC curve), in which the vertical axis represents the sensitivity (the ratio of correct discrimination of the group of above the MMSE N point) and the horizontal axis represents 1-specificity (the ratio of correct discrimination of the group of less than the MMSE N point), and selecting the threshold at the point (black circle in the figure) which is closest to the upper-left point (white circle in the figure, ideal discrimination accuracy) in a straight line. Further, when the frequency distribution of the two groups appears in a histogram with two peaks, there is a method of selecting the bottom of the valley of the histogram as a threshold. Or, there is also a method of setting the threshold to a value maximizing the between-group variance when the frequency distribution is divided into two groups by a certain threshold. As shown in FIG. 10A, the threshold $Y_{th}$ of the discrimination index for discriminating two groups divided by different thresholds of MMSE varies, such as $Y_{tha}$ and $Y_{thb}$, depending on the threshold of MMSE. Thus, the thresholds $Y_{th1}$ to $Y_{th2}$ in FIG. 10C also correspond to the thresholds 1 to 29 of MMSE.

Further, the evaluation accuracy database 45 stores the discrimination accuracy AUC in the case of discriminating between the two groups that are discriminated by different thresholds of MMSE. In the example of FIG. 10C, it can be found that the discrimination accuracy AUC is the maximum when the threshold of MMSE is 27. The discrimination accuracy can also be evaluated by an index other than AUC, such as, for example, sensitivity or specificity. In the case of AUC, the thresholds $Y_{th1}$ to $Y_{th2}$ are not required because the discrimination accuracy in all thresholds is comprehensively evaluated by shifting the threshold from the minimum value of the histogram to the maximum value. On the other hand, in the case of sensitivity and specificity, the discrimination accuracy is calculated using the thresholds $Y_{th1}$ to $Y_{th2}$.

FIG. 10D is an example of the task execution order data 44A in two-group discrimination, which is generated based on the evaluation accuracy database 45, showing the threshold Nmax that maximizes AUC corresponding to each task name (or possibly task ID, or the like). The threshold Nmax shown here is MMSE that can perform two-group discrimination with the highest degree of accuracy in each task. The type of each task can be identified, for example, by name or ID. According to FIG. 10D, it can be found that one hand metronome is good at performing two-group discrimination at a boundary of 27 points on the borderline between normal control and mild cognitive impairment. Then, it can be found that both hand alternate free run is good at performing two-group discrimination at a borderline of 22 points near the borderline between mild cognitive impairment and cognitive impairment. It can be found that both hand simultaneous free run as well as one hand free run are good at performing two-group discrimination at boundaries of 17 points and 15 points, respectively, and thus good at discriminating between very severe cognitive patients and milder cognitive patients. In this way, the severity score capable of discriminating between two groups at a high degree of accuracy in each task is referred to as the optimum severity score. In this example, the score with the highest accuracy in each task is selected as the optimum severity score. However, it is also possible to select a severity score at which a greater discrimination accuracy than a predetermine discrimination accuracy was obtained.

As described above, in two-group discrimination, the generation device 1 was able to arrange the tasks ranging from the task good at performing two-group discrimination on severe patients to the task good at performing two-group discrimination on mild patients/normal control subjects, in order of severity as shown in FIG. 10D. This list is stored in the task execution order data 44A. The formula for obtaining the discrimination index from the characteristic quantity that can be obtained from each task, as well as the processing method are stored in the task execution order data 44A. At this time, as described below, thresholds $Y_{th1A}$ to $Y_{th4A}$ for performing two-group discrimination by the discrimination index are also recorded for the application of two-group discrimination to a new subject. This threshold is the threshold of the discrimination index corresponding to the threshold of MMSE. In the examples of FIG. 10C and FIG. 10D, the discrimination index threshold $Y_{th1A}$ and the discrimination index threshold $Y_{th27}$, both corresponding to Nmax=27 of one hand metronome, are equal to each other.

Further, the severity direction, positive or negative, is also recorded so as to determine which side of positive and negative of the threshold is severe. For example, in the example shown in FIG. 10A (a) (b), the negative side of the discrimination index threshold is severe. However, the magnitude of MMSE may reverse before and after the threshold, so that it is necessary to identify positive and negative in the severity direction.

Note that this example shows one point of the threshold Nmax at which AUC is the maximum in each task. However, it may also be possible to specify a range of severity in which discrimination accuracy is high by using other means. For example, there could be a case of listing all cases in which AUC is equal to or above a predetermined value. Further, although the discrimination accuracy is evaluated by shifting N in increments of one point, it is also possible to evaluate the discrimination accuracy by shifting N in increments of two points or larger.

<1-9-2. Case of Severity Estimation>

The following describes the case of estimating the severity score by task. Similar to two-group discrimination, a plurality of tasks is given, and a database obtained by measuring each task for a large number of subject groups is prepared and stored in the subject group task database 46. Further, the score evaluating cognitive/motor function in the same subject group is also obtained in advance.

Now, consideration is given to estimating the value of MMSE of a subject group from finger tapping data in a severity range of N to N+1 in increments of one point of MMSE. In order to estimate the MMSE, the characteristic quantity of finger tapping is used. Similar to two-group discrimination, one of the 47 characteristic quantities may be selected as a regression index, or one regression index may be calculated from a plurality of characteristic quantities by statistical methods such as main component analysis and multiple regression analysis. The relationship between regression index and MMSE is fit to a line or curve by using linear regression analysis or other optimization methods. At this time, the data to be fit is not the data in the range of N to N+1 points, but all data are used. The range of N to N+1 points is targeted only in the evaluation of the regression accuracy.

Figure 11A:
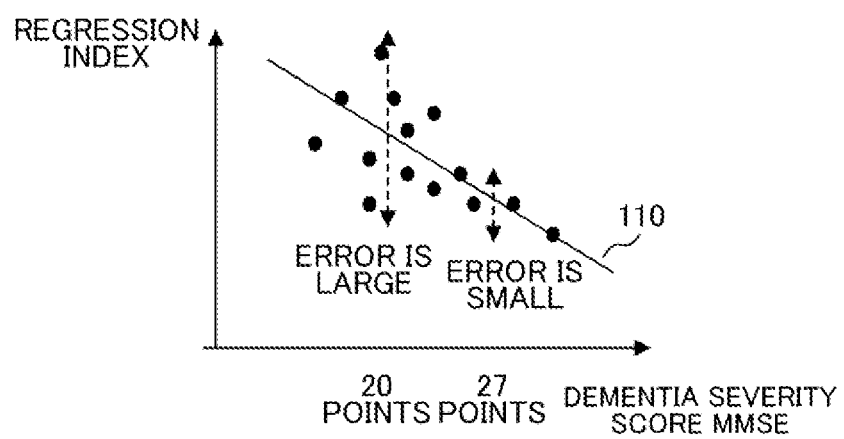
FIG. 11A is a graph showing the relationship between characteristic quantity and MMIS in the first embodiment.

FIG. 11A is a graph in which the horizontal axis represents MMSE and the vertical axis represents the regressions index in a certain task, showing one (person) sample as one black circle. As shown in FIG. 11A, the following considers the case of estimating the value of MMSE of the subject group from finger tapping data in the severity range of N to N+1 in increments of one point of MMSE, in each task. In this figure, when the MMSE value N is 20 points, the black circles are scattered widely from a regression line or curve 110 and the estimation error is large. On the other hand, when the MMSE value N is 27 points, the estimation error is small. In this way, the regression accuracy may vary when the severity range varies, even if the characteristic quantity is the same.

The regression accuracy showing the difference between good and bad of this fitting is evaluated by mean square error. The smaller the mean square error the higher the regression accuracy is. The regression accuracy may be evaluated by indices other than the mean square error, such as Akaike information criterion (AIC) and Bayesian information criterion (BIC).

In each task, the range of N to N+1 points is estimated by the regression index by changing the value of MMSE in increments of one point, to calculate the mean square error which is the regression accuracy at this time.

By the process described above, it is possible to generate the evaluation accuracy database 45 from the subject group task database 46. The specific process is the same as the flow shown in FIG. 10B. However, in the case of severity estimation, step S107 is replaced by the calculation process of the mean square error which is the regression accuracy. Further, in step S108, the regression accuracy is registered, instead of AUC, into the evaluation accuracy database 45.

FIG. 11B is a schematic diagram showing Nmax at which the mean square error is minimized, namely, the regression accuracy is maximized in the severity score estimation in each task. Here, the severity score can be estimated with the highest degree of accuracy in the range of Nmax to Nmax+1 in each task. As described above, the severity score that can estimate the severity score with a high degree of accuracy in each task is referred to as the optimum severity score. In this example, the severity score with the highest accuracy in each task is selected as the optimum severity score. However, it is also possible to select a severity score with which a regression accuracy greater than a predetermined given regression accuracy was obtained.

As described above, in severity estimation, it is possible to arrange the tasks in order from the task good at performing severity discrimination on severe patients to the task good at performing severity discrimination on mild patients/ normal control subjects, as shown in FIG. 11B, based on the evaluation accuracy database 45. This list is stored in the task execution order data 44B. This example evaluates the regression accuracy in the range of N to N+1 points. However, it is also possible to evaluate the regression accuracy in a wider range of points, such as N to N+2 points. In addition, although the regression accuracy is evaluated by shifting N in increments of one point, it is also possible to evaluate the regression accuracy in increments of two points or larger. Similar to FIG. 10D, the formula for obtaining the regression index from the characteristic quantity that can be obtained from the task, as well as the processing method are stored in the task execution order data 44B. In the process described above, it is also possible to perform two-group discrimination for discriminating between the group of less than Nmax and the group of above Nmax, with the value of Nmax as the threshold. Thus, similar to the case of two-group discrimination, discrimination thresholds $Y_{th1B}$ to $Y_{th4B}$ are recorded in advance. Further, positive or negative in the severity direction is also recorded in advance for each of the discrimination thresholds $Y_{th1B}$ to $Y_{th4B}$.

1-10. Task Selection Method

The following describes a method of selecting a task that the subject is asked to measure, from the task execution order data 44. The task execution order data is a list in which tasks are arranged in order from the task good at estimating severe patients to the task good at estimating mild patients, as shown in FIGS. 10D and 11B.

1-10-1. Case of Two-Group Discrimination

Figure 12:
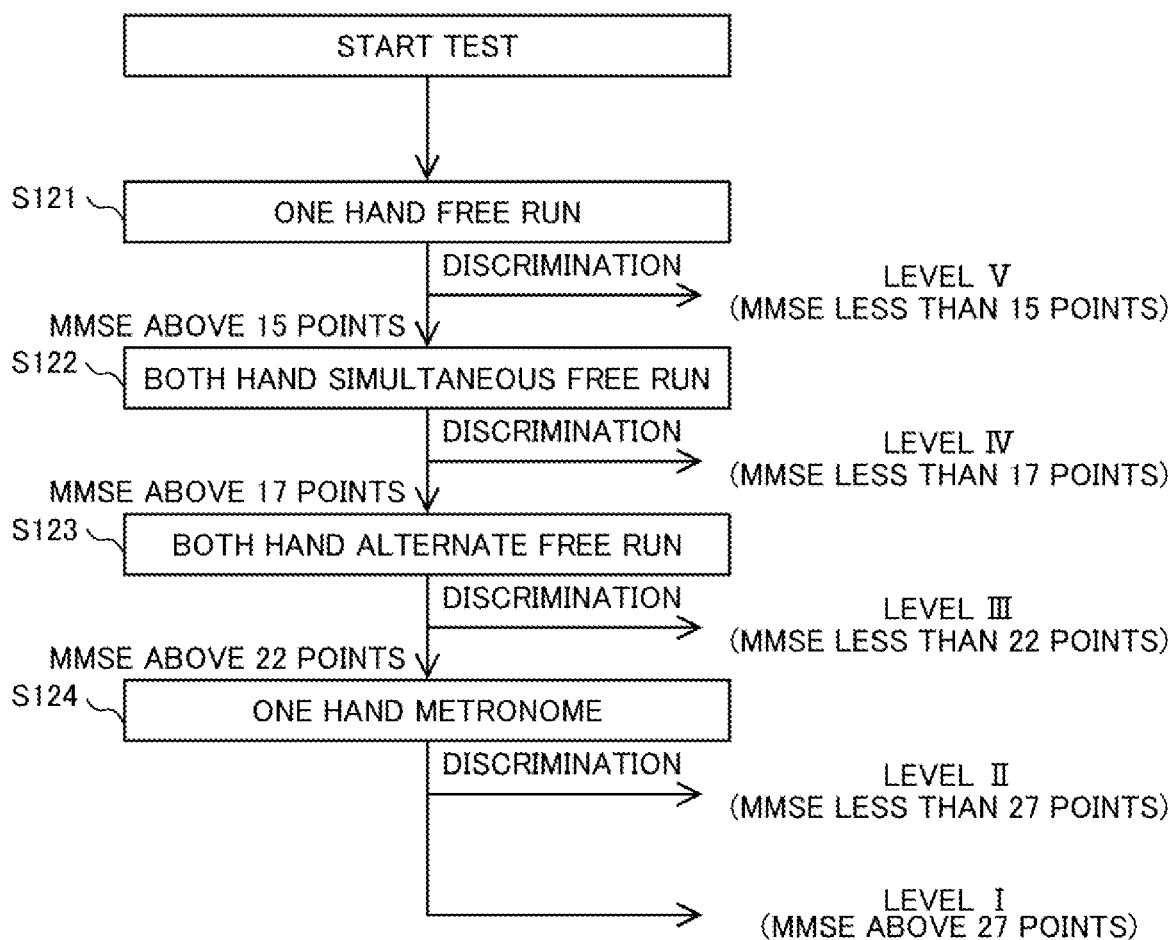
FIG. 12 is a flowchart showing the flow of the task execution order in two-group discrimination, according to the first embodiment.

A method of selecting tasks is described with reference to the flowchart in FIG. 12. FIG. 12 shows a selection method of tasks in the case of using the task execution order data 44A shown in FIG. 10D.

First, in step S121, the process performs the measurement of the test measures the task good at evaluating the most severe patients (one hand free run) on all subjects. Here, the process calculates the characteristic quantity of the measurement data of this finger tapping, and then calculates the discrimination index by substituting the characteristic quantity into the equation recorded in the list stored in the evaluation accuracy database 45.

The process checks whether the discrimination index of the subject is greater or smaller than a predetermined threshold recorded in the list stored in the evaluation accuracy database 45. When the discrimination index is smaller than the threshold and the severity direction is −1, or when the discrimination index is greater than the threshold and the severity direction is 1, it is determined that the subject is a severe patient by the screening test in this task. Thus, the test ends here. On the other hands, when the discrimination index is greater than the threshold and the severity direction is −1, or when the discrimination index is smaller than the threshold and the severity direction is 1, the subject clears the screening test in this task. Thus, the process proceeds to the next task. In the example of FIG. 10D, the severity direction of one hand free run is 1. Thus, when the determination index is greater than the threshold, it is determined that the subject is a severe patient of less than MMSE 15 points, and the process ends the test. When the discrimination index is smaller than the threshold, the subject is determined to be a severe patient of above NNSE MMSE 15 points, and the process proceeds to the next task.

As the next task in step S122, the process performs the measurement of the task good at evaluating mild patients (both hand simultaneous free run). This task is the task good at evaluating a subject close to the next severe level though not to the extent of one hand free run. The subsequent evaluation is the same as in one hand free run. When the discrimination index is smaller than the threshold and the severity direction is −1, or when the discrimination index is larger than the threshold and the severity direction is 1, it is determined that the subject is a severe patient by the screening test in this task, and the determination ends here. On the other hand, when the discrimination index is larger than the threshold and the severity direction is −1, or when the discrimination index is smaller than the threshold and the severity direction is 1, the subject clears the screening test in this task. Thus, the process proceeds to both hand alternate free run which is the next step S123.

In this way, the process performs the tasks described in the task execution order data 44A, sequentially, in step S123 and S124 and repeats the steps until the determination by the discrimination index is completed. The last subject group to be determined as belonging to the severe side is the normal control group.

1-10-2. Case of Severity Estimation

Also in the case of severity estimation, similar to the two-group discrimination, the determination is completed with a small number of tasks for severe patients. As for mild patients and normal control subjects, the process performs the determination with a larger number of tasks.

Figure 13:
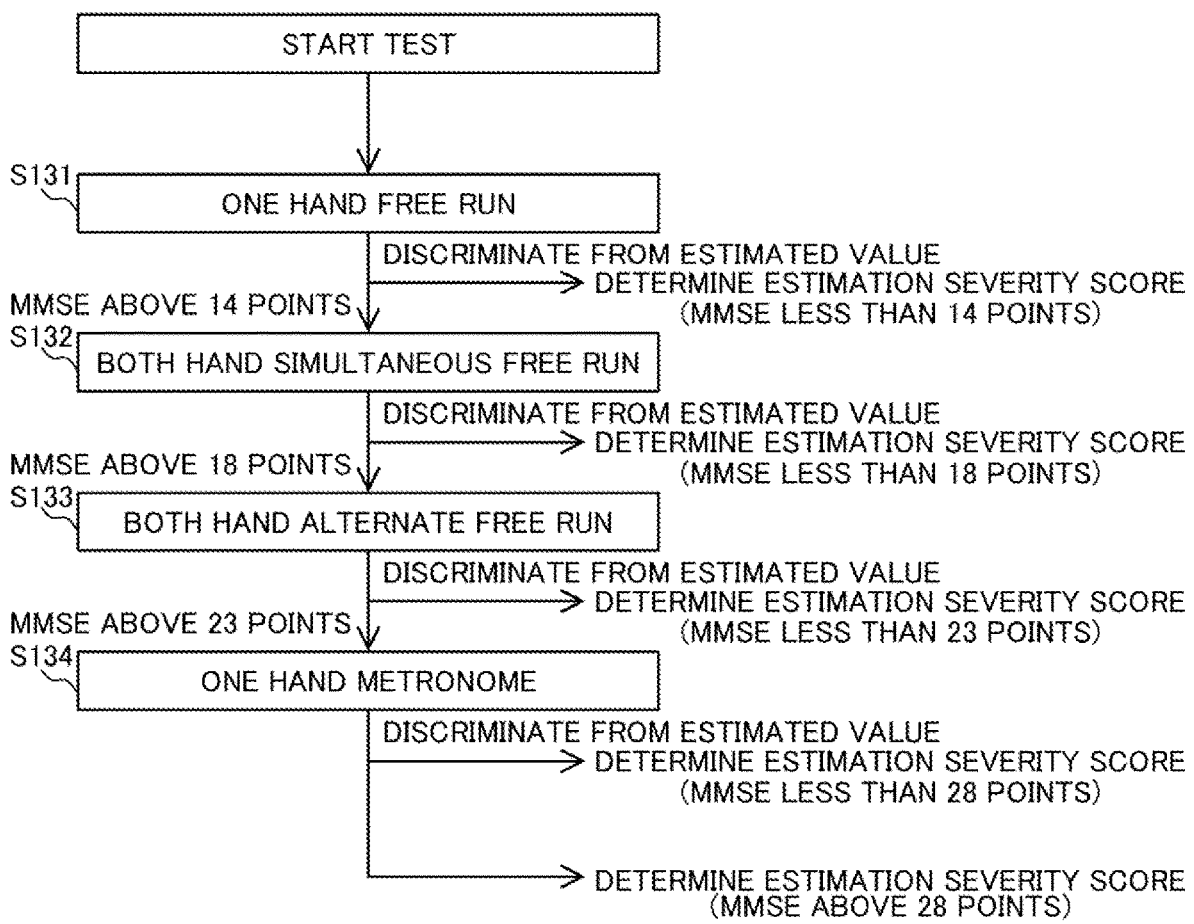
FIG. 13 is a flowchart showing the flow of the task execution order in severity score estimation, according to the first embodiment.

A basic task selection method is described with reference to FIG. 13. FIG. 13 shows a task selection method in the case of using the task execution order data 44B in FIG. 11B. First, in Step S131, the process performs the measurement of the task good at evaluating the most severe patients (one hand free run) on all subjects. Here, the process calculates the characteristic quantity of the measurement data of this finger tapping, and calculates the regression index by substituting the characteristic quantity into the equation recorded in the list stored in the evaluation accuracy database 45.

The process checks whether the regression index of the subject is greater or smaller than a predetermined threshold recorded in the list stored in the evaluation accuracy database 45. When the discrimination index is smaller than the threshold and the severity direction is —1, or when the discrimination index is greater than the threshold and the severity direction is 1, it is determined that the subject is a severe patient by the screening test in this task. Thus, the test ends here. On the other hands, when the discrimination index is greater than the threshold and the severity direction is −1, or when the discrimination index is smaller than the threshold and the severity direction is 1, the subject clears the screening test in this task. Thus, the process proceeds to the tasks in step S132 and subsequent steps.

In this way, similar to the case in FIG. 12, the process performs the tasks described in the task execution order data 44B, sequentially, in steps S132 to S134 and repeats until the determination by the discrimination index is completed. Note that the difference from the two-group discrimination is that the severity estimation can not only perform classification but also calculate the estimated score.

1-10-3. Others

The above description has focused on the method of selecting tasks without using the subject's prior information. However, it is also possible to select tasks by using personal information and past evaluation results of the subject.

For example, when the severity score rated by the subject's doctor is previously given, the process may start with the task good at evaluating the severity close to the given score. Further, also in the case of having past evaluation results of hand movement task, the process may start with the task good at evaluating the severity close to the score of the past evaluation results. In such a case, if the task is not well done, the process returns to the task for more severe subjects and measures the task. If the task is well done, the process measures the task for milder subjects. In this way, the process measures an appropriate task while proceeding or returning in the flow in FIG. 12 and in FIG. 13.

In other words, for example, when the past severity score of the subject is MMSE 18 in FIG. 12, the process starts with the task of both hand simultaneous free run (S122), which has the closest optimum severity score MMSE 17. As a result of the task of both hand simultaneous free run (S122), when the estimated severity score indicates more severe than the optimum severity score MMSE 17 of both hand simultaneous free run, the process performs one hand free run (S121) which is the task with the optimum severity score indicating more severe state, or ends the task. On the other hand, as a result of the task of both hand simultaneous free run, when the estimated severity score indicates less severe than the optimum severity score MMSE 17 of both hand simultaneous free run, the process performs both hand alternate free run (S123) which is the task with the optimum severity score indicating less severe state. In this way, it is possible to sequentially select tasks with which optimum determination can be performed on the subjects.

1-11. Screen Display 1-11-1. Screen Display (1)—Menu

The following describes the display screen on which the measurer operates the terminal device 4. In general, a menu screen, which is an initial screen of the service, is first displayed. The menu screen has a subject information field, an operation menu field, a setting field, and the like.

In the subject information filed, the subject information can be input and registered by the measurer. Note that if the subject information recorded in the electronic health record or the like is already present, it may be possible to cooperate with this subject information. Examples of the subject information that can be input are subject ID, name, birth date or age, gender, dominant hand, disease/condition, note, and the like. The dominant hand can be input by selecting from right hand, left hand, both hands, unknown, and the like. The disease/condition can be input, for example, by selecting from options of a list box, or can be input in an arbitrary text.

The operation menu field displays operation items of the function that the service provides. The operation items include "calibration", "perform hand movement measurement (task)", "perform finger movement training", "see evaluation results", "end", and the like. When "calibration" is selected, the calibration, namely, the process of adjustment of the motion sensor 20, or the like, is performed on the subject's hand. The state of whether it is adjusted or not is also displayed. When "perform hand movement measurement (task)" is selected, the screen transits to a task measurement screen to analyze the state of the motor function or the like of the subject. When "perform hand movement training" is selected, the screen transits to a training screen by omitting task measurement. When "see evaluation results" is selected, the screen transits to an evaluation result screen when analysis evaluation results are already given. When "end" is selected, the service is ended.

1-11-2. Display Screen (2)—Task Measurement

After the menu display, for example, a task measurement screen is shown. This screen displays task information. For example, the screen displays a graph, in which the horizontal axis represents the time and the vertical axis represents the distance between two fingers, with respect to each of the right and left hands. Other instruction information can also be output on the screen to explain the task content. For example, it is possible to provide an area of a video that explains the task content with video and audio. The screen includes operation buttons such as "Start Measurement", "Redo Measurement", "End Measurement", "Save (registration)", and the like. The measurer can select these buttons. The measurer selects "Start Measurement" to perform the movement of the task, according to the task information on the screen. The measurement device 3 measures the movement of the task to obtain a waveform signal. The terminal device 4 displays the measured waveform corresponding to the waveform signal being measured, in real time, as a graph. The measurer selects "End Measurement" after the movement, and selects "Save (registration)" when determining the data. The measurement device 3 transmits the task measurement data to the generation device 1.

1-11-3. Display Screen (3)—Evaluation Task

Figure 14:
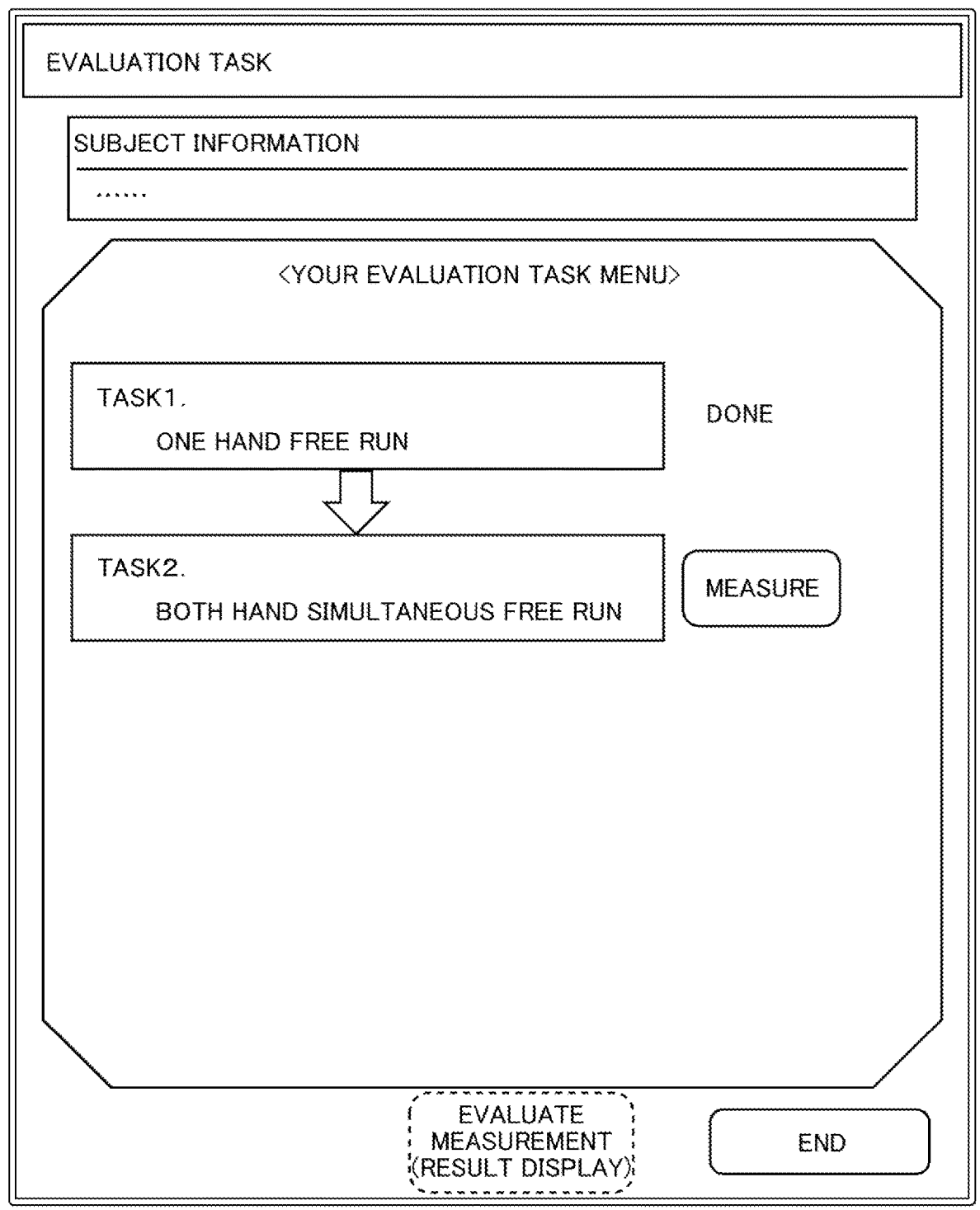
FIG. 14 is a plan view showing an evaluation task screen as an example of the display screen in the first embodiment.

FIG. 14 is a screen showing the evaluation task having been completed in order to show the progress of the test to the subject.

1-11-4. Display Screen (4)—Evaluation Results

Figure 15:
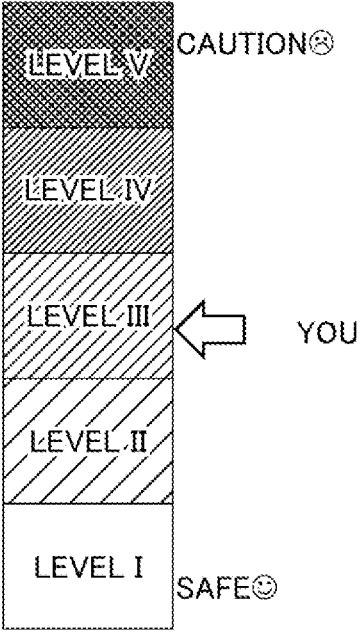
FIG. 15 is a plan view showing an evaluation result screen (two-group discrimination) as an example of the display screen in the first embodiment.

As another example, FIG. 15 shows an evaluation result screen in the case of selecting a task by two-group discrimination. This screen is a screen for showing evaluation results to the subject. This screen displays the analysis evaluation result information of the task. In two-group discrimination, the subjects are sorted into groups divided by a threshold set in each task. Thus, the evaluation results are displayed for each level as shown in the figures. This screen is automatically displayed after the analysis evaluation of the task. This example shows the case of displaying the evaluation results for levels I to V in a bar graph. The evaluation value may be converted into 20 points, 40 points, and so on, and displayed in the form of performance score (for example, the perfect score is 100 points) or other form, instead of being classified into each level. In addition to the graph of the evaluation value, evaluation comments or other references related to the analysis evaluation result may also be displayed. The analysis evaluation part 13 generates the evaluation comments. For example, the following messages are displayed: "Good result" "Better than before". The screen includes operation buttons such as "Overlay past results" and "End". When "End" is selected, the generation device 1 switches the screen to the initial screen.

Figure 16:
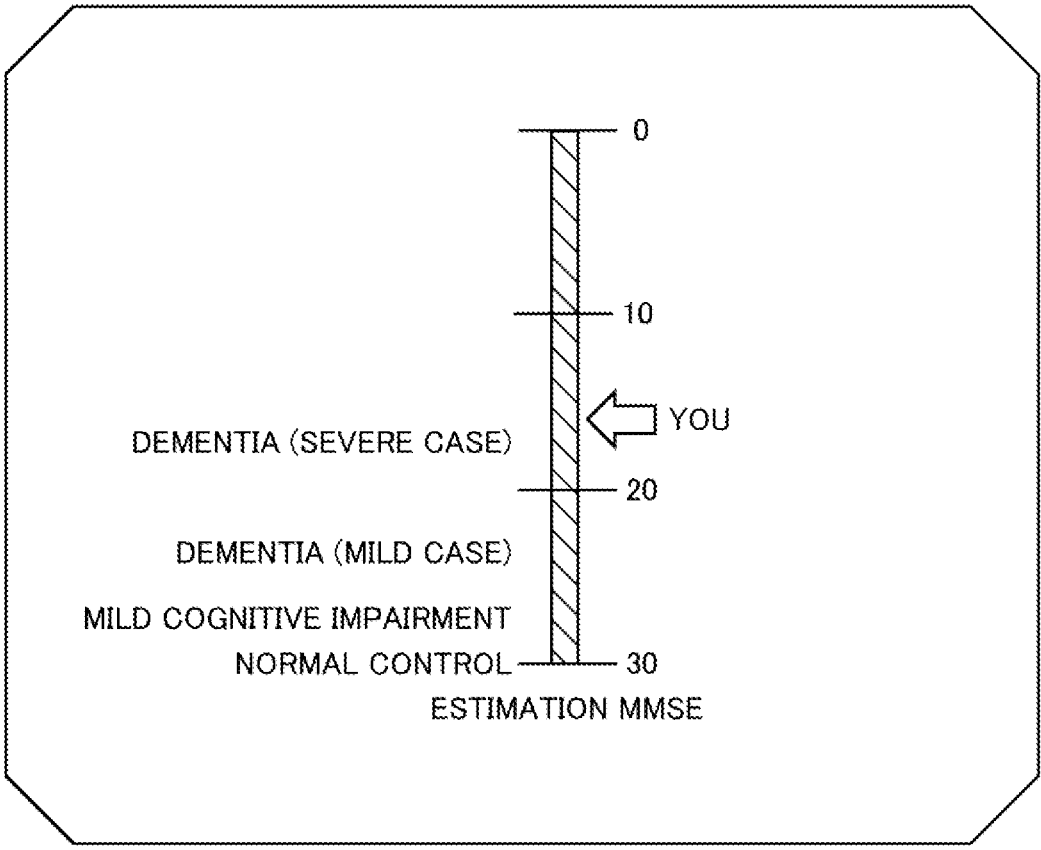
FIG. 16 is a plan view showing an evaluation result screen (severity estimation) as an example of the display screen in the first embodiment.

FIG. 16 shows the evaluation result screen in the case of selecting a task by severity score estimation. This screen is a screen for showing the evaluation result to the subject. In severity estimation, the estimated score of the severity of the subject is also calculated, so that the evaluation result is displayed on the same scale as MMES.

FIG. 17 is a screen on which the measurer such as health care professional or caretaker checks the progress of the task measurement as well as the evaluation results. This screen shows task completed/uncompleted, the evaluation results of tasks having been measured, and the like. The task execution order is automatically generated. However, when requiring reduction in measurement time, the measurer can forcibly end the task by pressing the "End" button. In this case, the evaluation results are displayed by using only the tasks having been measured.

Note that in this example, the measurer performs the screen operation to measure the subject's hand movement. However, the measurer and the subject may be the same person. In this case, the person can self-check the cognitive/motor function by the test.

1-12. Effects and the Like

As described above, according to the execution order determination system of the first embodiment, it is possible to achieve both reduction of measurement load on the subject as well as accuracy improvement in evaluation results, by determining and presenting the optimum execution order of a plurality of hand movement tasks for evaluating human cognitive and motor functions. More specifically, a subject who is determined to be severe from the beginning requires to measure only one task, so that the measurement load is reduced. Further, in the case of a subject who is difficult to evaluate between mild and normal control, the amount of information increases due to a plurality of task measurements, allowing for a highly accurate test.

Example 2

A task execution order determination system according to Example 2 (second embodiment) of the present invention is described with reference to FIG. 18 to FIG. 21. The basic configuration of the second embodiment is the same as the first embodiment. Thus, the following describes only parts in the configuration of the second embodiment different from the configuration of the first embodiment.

2-1. System (2)

Figure 18:
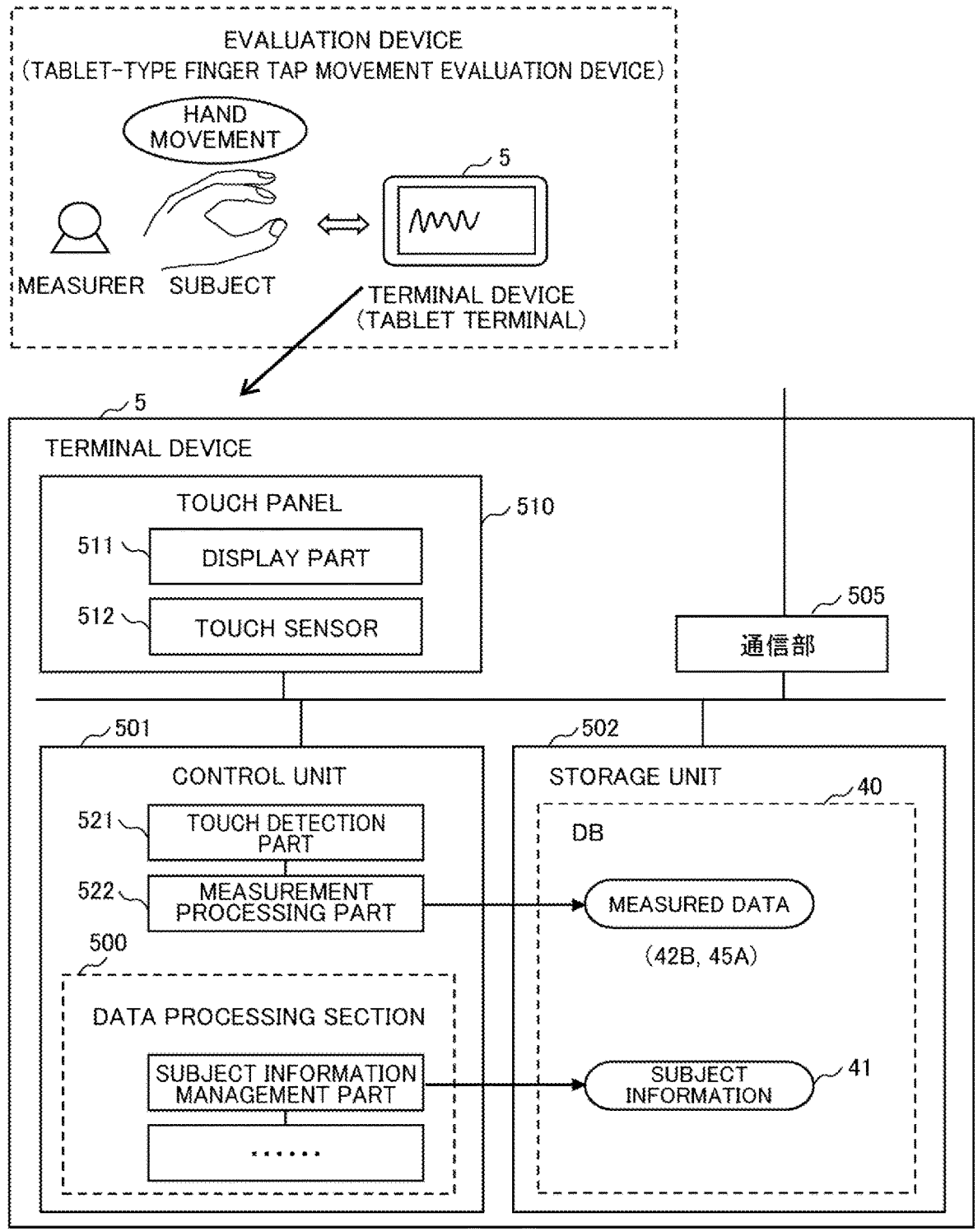
FIG. 18 is a block diagram showing the configuration of a task execution order determination system according to a second embodiment of the present invention.

FIG. 18 shows the configuration of a hand movement evaluation system including the task execution order determination system of the second embodiment. The hand movement evaluation system is provided in a facility, subject's home, or other location. The task execution order determination system of the second embodiment uses an evaluation device which is a tablet-type finger tap movement evaluation device. The evaluation device is configured with a terminal device 5 which is a tablet terminal. In the second embodiment, the motion measurement and information display are performed using a touch panel provided in the terminal device 5. The second embodiment corresponds to the configuration in which the measurement function of the measurement device 3 as well as the display function of the terminal device 4 in the first embodiment are integrated into one terminal device 5. The terminal device 5 may be provided in a facility or may be owned by the subject.

The terminal device 5 has a control unit 501, a storage unit 502, a communication unit 505, and a touch panel 510, all of which are connected by a bus. The touch panel 510 has a display part 511 and a touch sensor 512. The display part 511 is, for example, a liquid crystal display part or an organic EL display part, and has a display screen. The touch sensor 512 is, for example, a capacitance type sensor provided in the area corresponding to the display screen. The touch sensor 512 detects a capacitance change, as an electrical signal, depending on the state in which fingers approach or contact and contact on the display screen, and outputs the detected signal to the touch detection part 521.

The control unit 501 controls the whole terminal system 5. The control unit 501 is configured with CPU, ROM, RAM, and the like, and achieves a data processing section 500 that performs task execution order determination processing or other operations, based on software program processing. The configuration of the data processing section 500 is substantially the same as that of the first embodiment. The control unit 501 also has a touch detection part 521 and a measurement processing part 522. The control unit 501 achieves a function for obtaining measurement data through the touch panel 510, a function for processing and analyzing the measurement data, a function for outputting information to the display screen of the display part 511 of the touch panel 510, and the like. The touch detection part 521 performs a process of detecting the state of the subject's fingers approaching or contacting on the display screen, as well as the finger movement state, as touch position coordinates and the time-series signal, based on the detection signal from the touch sensor 512. The measurement processing part 522 measures the position and movement of the fingers on the display screen as a waveform signal by using the detection information of the touch detection part 521, and obtains the result as measurement data. The data processing section 500 determines the task execution order based on the measurement data by the same process as the first embodiment, and displays on the display screen of the display part 511. Further, the data processing section 500 generates analysis evaluation data or other information, and displays the evaluation screen or other screen on the display screen of the display part 511.

2-2. Movement, Display Screen Example (1)

FIG. 19 shows a method of performing the movement of finger tapping on the display screen 210 of the terminal device 5. The terminal device 5 may provide a task using this method. In this method, the control unit 501 displays an area 211 for arranging two target fingers of each hand on the background area of the display screen 210. For example, this figure shows the case in which the first finger is the thumb and the second finger is the index finger. The subject places two fingers of each hand in contact or approach state on the area 211. Although depending on the touch sensor 512 or the like, this example basically maintains the state in which the fingers touch the area 211 of the display screen. The subject performs finger tapping with the two fingers opening and closing in the area 211. The terminal device 5 measures the movement of finger tapping through the touch sensor 512 or other device, and obtains measurement data such as a waveform signal in the same way as in the first embodiment. The movement 212 of the first finger and the movement 213 of the second finger on the area 211 are shown by the arrows. Assuming the distance between the two fingers is L, L1 represents the distance on the left hand side and L2 represents the distance on the right hand side.

As an example of the measurement data corresponding to the finger tapping movement, the waveform signal of the distance D between the two fingers can be obtained as described above in FIG. 7. Similar to the first embodiment, the terminal device 5 extracts the characteristic quantity based on the measurement data by the method described above.

2-3. Movement, Display Screen Example (2)

FIGS. 20(A) and 20(B) are plan views showing a reaching method as another example of the finger tapping movement and the display screen. The terminal device 5 may provide a task using the reaching method. FIG. 20(A) is a plan view showing cross reaching. First, a graphic 231 of the initial position is displayed on the display screen 210 of the terminal device 5. Then, a measurement is started measurement in a state in which the target finger, for example, the index finger, is placed on the graphic 231 of the initial position. After the start of the measurement, a graphic 232 of the target corresponding to a marker, for example, a cross is displayed on the display screen 210. The control unit 501 displays the graphic 232, for example, at different positions at predetermined time intervals. The subject performs finger tap by extending the hand to track the position of the graphic 232. This example shows the state in which the finger taps on a position 233 deviating from the center position of the graphic 232. There is a distance E corresponding to the deviation between the center position of the target graphic 232 and the position 233 of the tap or touch. The terminal device 5 calculates the distance E, delay time TD, and the like as one characteristic quantity, based on the measurement data. The delay time TD is the time from when the target graphic 232 is displayed in a waiting state in which the finger is placed on the graphic 231 of the initial position to when the finger touches the target graphic 232.

FIG. 20(B) is a plan view showing circle reaching. A circular area is shown as a target graphic 234. The subject similarly performs finger tap on the circular area of the graphic 234. For example, the distance between the center position of the graphic 234 and the tap position is extracted as a characteristic quantity.

2-4. Movement, Display Screen Example (3)

A continuous touch method is shown as still another example of the finger tapping movement and the display screen. The terminal device 5 may provide a task using the continuous tach method. As an example of the continuous touch method, for example, one hand continuous touch performed by one hand is shown here. A graphic to be touched by the left thumb, for example, a circular area, is displayed in one part, for example, a left lower part of the display screen 210. The subject touches the displayed graphic with the finger and tries to continue touching. When the graphic changes to non-display state, the subject releases the finger from the graphic. The control unit 501 controls the display of the graphic. For example, the graphic is switched between display and non-display at predetermined time intervals, and is displayed at a predetermined number of times. Further, in addition to displaying the graphic, auditory stimulation or other factors may also be given as instruction information. As the characteristic quantity, for example, the number of touches, the touch interval, the touch delay time, and the like, are extracted.

Further, both hand simultaneous continuous touch, which is performed with both hands, is shown as another example of the continuous touch method. Graphics showing touch positions of target fingers of the left and right hands are displayed in two parts of the display screen 210. The subject continuously touches the displayed graphics with both hands in simultaneous timing. Similarly, the subject can also perform both hand alternate continuous touch. In this case, the control unit 501 switches between the left and right graphics so that the graphics are displayed alternately. The subject touches these graphics with the left and right hands at alternate timings. For example, the difference between touch phases in the left and right graphics is extracted as a characteristic quantity. A predetermined index item, for example, both sides' cooperation is associated with the characteristic quantity. The ideal value of the phase difference is 0 degrees for both hand simultaneous continuous touch, and 180 degrees for both hand alternate continuous touch.

As another movement example, auditory stimulation or the like may be output as instruction information, without displaying the graphics. For example, it may be possible to output two types of sound at predetermined time intervals between the time when touch should be done and the time when touch should not be done.

2-5. Movement, Display Screen Example (4)

As another example of the finger tapping movement and the display screen, a tap method with light is shown. The terminal device 5 may provide a task using this method. For example, one hand tap performed with one hand is shown. A graphic for tap of the target finger of the left hand as well as a timing mark, which is light as visual stimulation to indicate the tap timing on the graphic, are displayed on the display screen 210. The control unit 501 displays the graphic blinking on and off. The subject taps the graphic for tap at the time when the timing mark is displayed. As another movement example, a method of outputting sound which is auditory stimulation, instead of the timing mark of visual stimulation, or a method of performing continuous touch may also be available. As the characteristic quantity, for example, there is a time lag at the time of tap or touch from the periodic occurrence of the stimulation. This time lag corresponds to the delay time from when the timing mark is displayed to when the graphic is tapped. Similarly, it is possible to perform both hand simultaneous tap. Two graphics for tap are provided on the left and right sides, and two timing marks as visual stimulation are displayed blinking at the same timing. Similarly, in the case of both hand alternate tap, the control unit 501 displays the two left and right timing marks blinking at alternate timings.

2-6. Movement, Display Screen Example (5)

Figure 21:
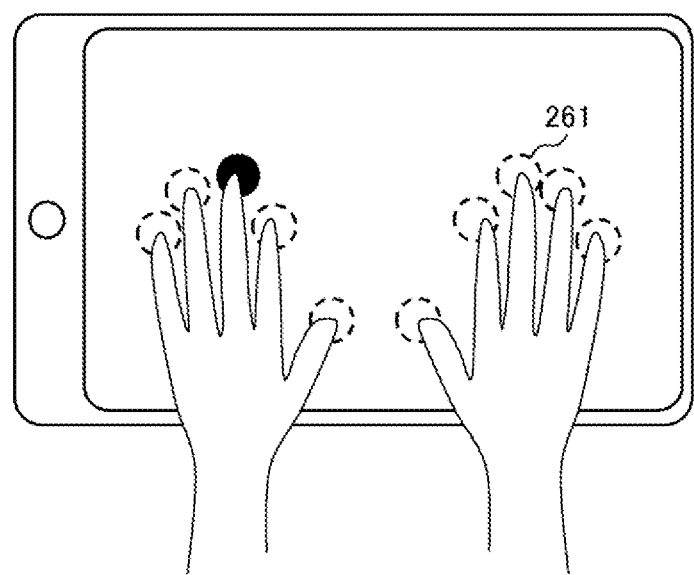
FIG. 21 is a plan view showing five-finger tap as a movement example in the second embodiment.

FIG. 21 shows a five-finger tap method as another example of the finger tapping movement and the display screen. The terminal device 5 may provide a task using the five-finger tap method. In this method, the five fingers of the target hand are used. The terminal device 5 displays a graphic 261 to be tapped with the five fingers of the respective hands, ten fingers in total, on the background area of the display screen 210. The subject first places the five fingers touching the display screen 210. The terminal device 5 automatically adjusts and sets the display positon of the graphic 261 based on the detection of the touch position. The terminal device 5 controls the display of the graphic 261 of each position. The terminal device 5 brings the graphic 261 of the position to be tapped into a specific display state (for example, indicated by a black circle), while bringing other graphics 261 of positions not to be tapped into a different display state. The terminal device 5 controls switching of the display state of the graphic 261. The subject taps the graphic 261 with the finger in response to the display of the graphic 261 to be tapped. This method can evaluate various types of index items with respect to each of the five fingers. As a result, it is possible to determine which finger should be particularly trained.

2-7. Characteristic Quantity

Examples of the characteristic quantity in the second embodiment are as follows.

The characteristic quantity parameters related to the reaching method are as follows. (2-1) "Average of delay time from target display" [sec] is the average with respect to the delay time. (2-2) "Standard deviation of delay time from target display" [sec] is the standard deviation related to the delay time.

(2-3) "Average of position error for target" [mm] is the average with respect to the distance E. (2-4) "Standard deviation of positional error for target" [mm] is the standard deviation with respect to the distance E.

The characteristic quantity parameters related to the one hand continuous touch method are as follows. (2-5) "Number of taps" [−], (2-6) "tap interval average" (sec), (2-7) "tap frequency" [Hz], (2-8) "tap interval standard deviation" [sec], (2-9) "tap interval variation coefficient" [−], (2-10) "tap interval variation" [mm$^2$], (2-11) "skewness of tap interval distribution" [−], (2-12) "local standard deviation of tap interval" [sec], (2-13) "tap interval decay rate" [−], and the like. The definition of each characteristic quantity is the same as that in the first embodiment.

The characteristic quantity parameters with respect to the both hand continuous touch method are as follows. (2-14) "Average of phase difference" [degree] is the average of the phase difference in the movement such as both hand touch. (2-15) "Standard deviation of phase difference" [degree] is the standard deviation of the phase difference.

The characteristic quantity parameters with respect to the method of touch and tap with light or sound stimulation are as follows. (2-16) "Average of time lag against stimulation" [sec] is the average of the time lag. (2-17) "Standard deviation of time lag against stimulation" [degree] is the standard deviation of the time lag.

2-8. Effects and the Like

As described above, according to the task execution order determination system of the second embodiment, similar to the first embodiment, it is possible to achieve both reduction of measurement load on the subject as well as accuracy improvement in evaluation results, by determining and presenting the optimum execution order of a plurality of finger movement tasks for evaluating human cognitive and motor functions. In particular, in the second embodiment, there is no need to provide the motion sensor 20 or other device.

2-9. Task Mixing

The first embodiment of the present invention uses only the task of finger tapping movement, and the second embodiment of the present invention uses only the task on the tablet terminal. However, it is also possible to use these tasks by mixing them together. For example, the task order execution data may also be generated in the following order: cross reaching (FIG. 20(A)), one hand continuous touch, and five finger tap (FIG. 21) on the tablet terminal, after one hand free run and both hand alternate free run in finger tapping. Further, it is possible to generate the task order execution data by using not only the hand movement task but also the movement task of other body parts. Further, tasks related to memory and cognitive tasks may be used together.

Example 3

A task execution order determination system according to Example 3 (third embodiment) of the present invention is described with reference to FIG. 22 to FIG. 24. The basic configuration of the third embodiment is the same as the first embodiment. The following will describe parts in the configuration of the third embodiment different from the configuration of the first embodiment.

1-3. System (3)

Figure 22:
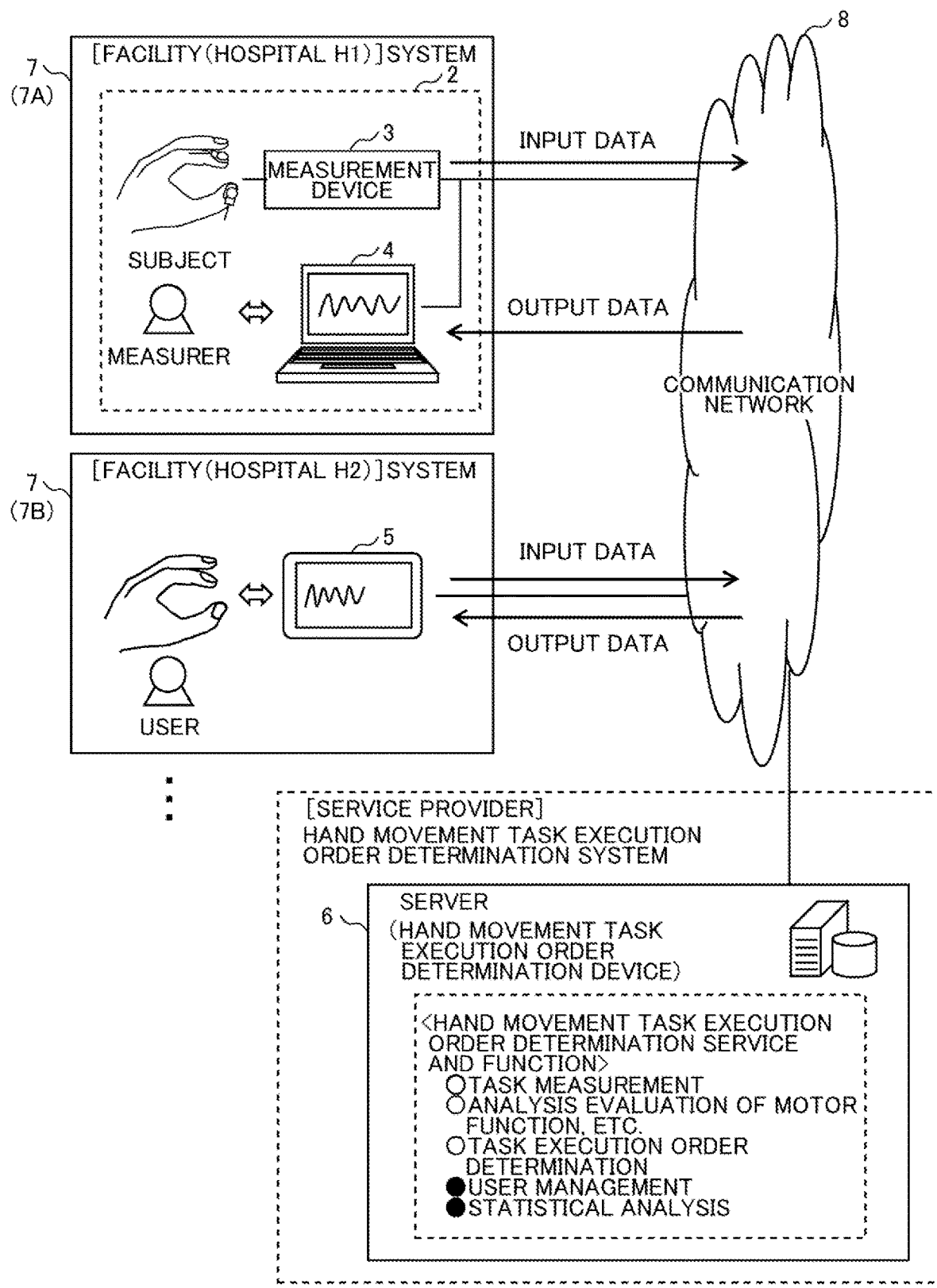
FIG. 22 is a block diagram showing the configuration of a task execution order determination system according to a third embodiment of the present invention.

FIG. 22 shows the configuration of a hand movement evaluation system including the task execution order determination system of the third embodiment. The hand movement evaluation system includes a service provider's server 6 and a plurality of facility systems 7, which are connected through a communication network 8. The communication network 8 and the server 6 may include a cloud computing system. The task execution order determination system of the third embodiment is mainly configured with the server 6. The server 6 corresponds to the task execution order determination device. A hand movement evaluation service is provided to a plurality of facility systems 7 by the server 6.

Various types of facilities are available, such as, hospitals and health examination centers, public facilities, amusement facilities and the like, or subject home. The system 7 is provided in each facility. The system 7 includes the evaluation device described above. As an example, the facility system 7 includes a system 7A of hospital H1, a system 7B of hospital H2, and the like. For example, the system 7A of hospital H1 has the measurement device 3 and the terminal device 4 that configure the evaluation device 2, similarly to the first embodiment. The system 7B of hospital H2 has the terminal device 5 that configures the evaluation device, similarly to the second embodiment. The configurations of the respective systems 7 may be the same or different from each other. The facility system 7 may include a hospital electronic health record management system or the like. The evaluation device of the system 7 may be a dedicated terminal. Subjects in the facility can evaluate the hand movement by using the evaluation device.

The server 6 is the device that the service provider administrates. The server 6 has a function to provide a hand movement evaluation service similar to the generation device 1 of the first embodiment, to facilities and subjects. The server 6 provides server processing to the evaluation device of the system 7 based on the client-server architecture model. In addition to such a function, the server 6 also has as a subject management function, a statistical analysis function, and the like. The subject management function is a function that manages subject information of a subject group, as well as data such as measurement data and analysis evaluation data, which are obtained through the facility systems 7, by registering and accumulating them in DB. The statistical analysis function is the function that performs statistical analysis processing and analysis processing on the subject group based on the subject information of the subject group as well as the analysis evaluation data, and the like. The server 6 generates a task examination order determination by using statistical analysis results, and presents tasks suitable for the subjects. Note that the terminal device 5 of the third embodiment does not require the function for generating the task execution order determination. The terminal device 5 includes a measurement function using a touch panel as well as a display function to display task execution order determination data or other information generated by the server 6.

3-2. Server

Figure 23:
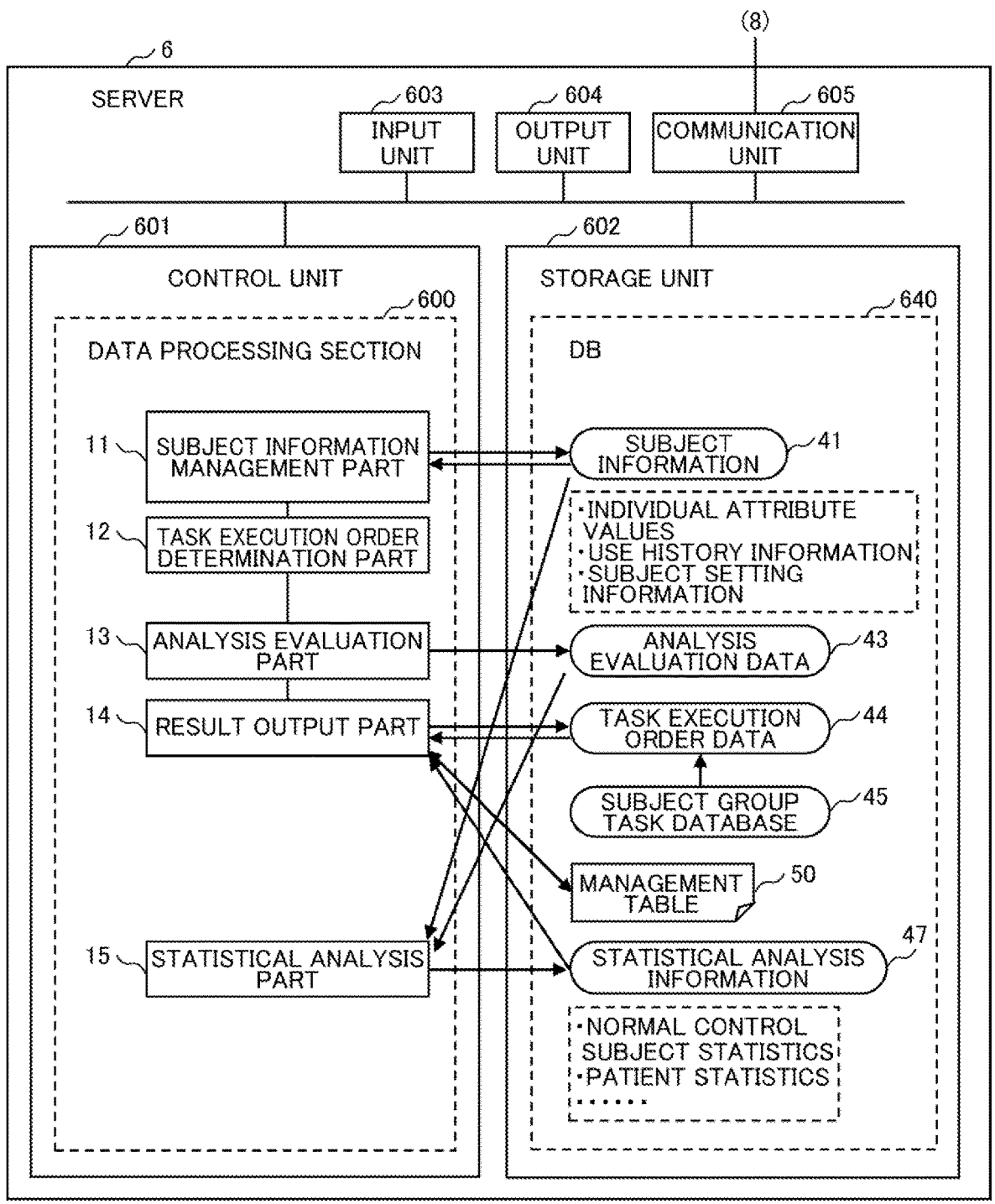
FIG. 23 is a block diagram showing the configuration of a server which is the task execution order determination device of the third embodiment.

FIG. 23 shows the configuration of the server 6. The server 6 includes a control unit 601, a storage unit 602, an input unit 603, an output unit 604, and a communication unit 605, all of which are connected through a bus. The input unit 603 is the part performing instruction input by the administrator or other users of the server 6. The output unit 604 is the part performing screen display, or the like, to the administrator or other users of the server 6. The communication unit 605 has a communication interface, performing communication processing with the communication network 8. A DB 640 is stored in the storage unit 602. The DB 640 may be managed by a DB server or the like other than the server 6.

The control unit 601 controls the whole server 6. The control unit 601 is configured with CPU, ROM, RAM, and the like, and achieves a data processing section 600 that performs hand movement task execution order generation or other operations based on software program processing. The data processing section 600 includes a subject information management part 11, a task execution order determination part 12, an analysis evaluation part 13, a result output part 14, and a statistical analysis part 17.

The subject information management part 11 registers subject information related to subject groups of the plurality of facility systems 7 into the DB 640, and manages the registered data as subject information 41. The subject information 41 includes attribute value, use history information, subject setting information, or other information for each individual subject. The use history information includes result information of a plurality of past evaluations for each subject. The statistical analysis part 17 performs statistical processing and analysis processing using the subject information 41 and the analysis evaluation data 43 or other information, and stores statistical analysis information 47, which is the result of the processing, into the DB 640. The statistical analysis information 47 includes normal condition subject statistics, patient statistics, or other statistical information.

3-3. Server Management Information

FIG. 24 shows an example of the data structure of the subject information 41 that the server 6 manages in the DB 640. The table of the subject information 41 includes subject ID, facility ID, on-site subject ID, gender, age, disease, severity score, condition, eyesight, hearing, history information, and the like. The subject ID is the unique identification information of the subject in this system. The facility ID is the identification information of the facility in which the system 7 is located. Note that other information, such as the communication address of the evaluation device of each system 7, is also managed. The on-site subject ID is the subject identification information when there is subject identification information managed in the facility or the system 7. In other words, the subject ID and the on-site subject ID are associated and managed. In the disease item and the condition item, values indicating disease and condition that the measurer, such as health care professional or caretaker, selected and input are store respectively. The severity score is a value indicating the degree related to disease.

The history information item is the information that manages the results of past service use by the subject, in which information such as the date and time of each use is stored in a time series. Further, in the history information item, the data such as the task execution order data performed in this trial as well as the analysis evaluation data are stored. The information of the address at which each data is stored may be stored in the history information item.

3-4. Statistical Analysis Processing

The statistical analysis part 15 performs statistical processing and analysis processing by referring to the subject information 41 registered in the DB 640 as needed, and generates the statistical analysis information 47. The statistical analysis part 15 refers, for example, to the group of normal control subjects. In other words, the statistical analysis part 15 refers to data of subjects with respect to whom a value indicating disease is not registered in the disease item of the attribute value in the subject information 41, or data of subjects with respect to whom a value indicating normal control is registered. The statistical analysis part 15 refers, for example, to the evaluation value of each index item of the analysis evaluation data 43 in the subject group. The statistical analysis part 15 sums up the evaluation value of each index item, calculates statistics such as average, and stores the obtained information including the statistics into the DB 640 as normal control subject statistical information. More specifically, the statistical analysis part 15 calculates statistics as normal control subject statistical information, according to the classification of the attribute values such as gender and age of the subjects. An example of the classification is male in his teens, twenties, and so on.

Similarly, the statistical analysis part 15 refers, for example, to the patient subject group. In other words, the statistical analysis part 15 refers to data of subjects with respect to whom a value indicating disease is registered in the disease item as the attribute value in the subject information 41. In particular, the subject group may be sorted according to the classification of disease (for example, "motor impairment" or the like). The statistical analysis part 15 refers, for example, to the evaluation value of each index item of the analysis evaluation data 43 in the subject group of the disease. The statistical analysis part 15 sums up the evaluation value of each index, calculates statistics such as average, and stores the obtained information including the statistics into the DB 640 as patient statistical information.

3-5. Effects and the Like

As described above, according to the task execution order determination system of the third embodiment, similar to the first embodiment, an appropriate order is generated to perform a plurality of tasks of hand movement in order to evaluate the motor function or cognitive function of the subject.

As a variation of the task execution order determination system of the third embodiment, the following configuration is available. In the first to third embodiments, the generation device 1, the terminal device 5, or the server 6 generated analysis evaluation data by performing analysis evaluation processing based on task measurement. As a variation, the system may also be configured to perform task measurement and analysis evaluation processing by an external device, and input the analysis evaluation data from the external device. For example, the server 6 obtains existing analysis evaluation data from the external device, and performs hand movement task execution order generation processing by using the analysis evaluation data.

The present invention has been described in detail based on preferred embodiments. However, the present invention is not limited to the specific embodiments and can be variously modified without departing from the scope of the present invention.

INDUSTRIAL APPLICABILITY

The present invention can be used in the information processing service technology for evaluating human cognitive and motor functions by a plurality of tasks of hand movement.

REFERENCE SIGNS LIST

1 . . . task execution order determination system,
2 . . . evaluation device,
3 . . . measurement device,
4 . . . terminal device.

The invention claimed is:

1. A method in a task execution order determination system including a processor and a storage device, the storage device storing task data of a plurality of different tasks performed by subjects to evaluate motor function and cognitive function of a current test subject by comparison of test results of a current test subject with test results of a group of test subjects previously tested, the method comprising:
storing in the storage device test results of the group of test subjects previously tested including scores of a characteristic quantity associated with the performance of each of the plurality of different tasks by each subject of the group of test subjects previously tested;
obtaining test results of the group of test subjects previously tested and of a currently tested subject with magnetic sensors that obtain hand motion data of the subject being tested for each of the plurality of different tasks,
wherein the magnetic sensors are coupled to an analog/digital conversion circuit that converts an analog waveform signal detected by the magnetic sensors into a digital waveform signal by sampling, the digital waveform signal is input to a motion sensor control part that includes an alternating current (AC) generation circuit, a current generation amplifier circuit, a preamplifier circuit, a detection circuit, an LPF circuit, a phase adjustment circuit, an amplifier circuit, and an output signal terminal, the motion sensor control part outputting a time-series waveform signal from which the characteristic quantity associated with the performance of the plurality of different tasks is obtained;
dividing the scores of the previously tested subjects into two groups, by discriminating between a first group of the previously tested subjects having a score less than a threshold N, N being an integer in a predetermined range of integers, and a second group of the previously tested subjects having a score equal to or more than the threshold N, based on an appearance frequency distribution with respect to the characteristic quantity of the first group and an appearance frequency distribution with respect to the characteristic quantity of the second group;
calculating a discrimination accuracy value (AUC) for each of a plurality of the thresholds N in the predetermined range corresponding to each reference task of the plurality of different tasks and storing a combination of the reference task and AUC value for each of the thresholds N for the predetermined range into an evaluation accuracy database;
selecting from the evaluation accuracy database one of the plurality of the thresholds N, for each reference task stored in the storage device, having a maximum accuracy value as a maximum accuracy value threshold Nmax; and
applying the maximum accuracy value threshold Nmax to the score of the characteristic quantity associated with the performance of the reference task by a current test subject to discriminate the score on the basis of the threshold Nmax and determine in which one of the first and second groups that the score of the characteristic quantity associated with the performance of the reference task is grouped as a representation of the motor function and cognitive function of a current test subject.

2. The method in a task execution order determination system according to claim 1, further including adding the score of the characteristic quantity associated with the performance of the reference task by the current test subject to the stored test results of the group of test subjects previously tested and updating the evaluation accuracy database to include the test results of the current test subject.

3. The method in a task execution order determination system according to claim 1, wherein each of the reference tasks is a hand movement task and a task execution order of the reference tasks is determined with respect to the threshold Nmax from a highest integer value of Nmax to lowest integer value of Nmax, which represents a range of reference tasks able to be performed by a test subject according to an order of severity of the test subject's cognitive/motor function.

4. The method in a task execution order determination system according to claim 1, wherein the step of calculating a discrimination accuracy value (AUC) for each of the thresholds N in the predetermined range for each reference task includes calculating a discrimination accuracy value (AUC) for each integer value of the thresholds N in the predetermined range of the thresholds N.

5. A method in a task execution order determination system including a processor and a storage device, the storage device storing task data of a plurality of different tasks performed by subjects to evaluate motor function and cognitive function of a current test subject by comparison of test results of a current test subject with test results of a group of test subjects previously tested, the method comprising:
storing in the storage device test results of the group of test subjects previously tested including scores of a characteristic quantity associated with the performance of each of the plurality of different tasks by each subject of the group of test subjects previously tested;

obtaining test results of the group of test subjects previously tested and of a currently tested subject with magnetic sensors that obtain hand motion data of the subject being tested for each of the plurality of different tasks;

wherein the magnetic sensors are coupled to an analog/digital conversion circuit that converts an analog waveform signal detected by the magnetic sensors into a digital waveform signal by sampling, the digital waveform signal is input to a motion sensor control part that includes an output signal terminal, the motion sensor control part outputting a time-series waveform signal from which the characteristic quantity associated with the performance of the plurality of different tasks is obtained;

dividing the scores of the previously tested subjects into two groups, by discriminating between a first group of the previously tested subjects having a score less than a threshold N, N being an integer in a predetermined range of integers, and a second group of the previously tested subjects having a score equal to or more than the threshold N, based on an appearance frequency distribution with respect to the characteristic quantity of the first group and an appearance frequency distribution with respect to the characteristic quantity of the second group;

calculating a discrimination accuracy value (AUC) for each of a plurality of the thresholds N in the predetermined range corresponding to each reference task of the plurality of different tasks and storing a combination of the reference task and AUC value for each of the thresholds N for the predetermined range into an evaluation accuracy database;

selecting from the evaluation accuracy database one of the plurality of the thresholds N for each reference task stored in having a maximum accuracy value as a maximum accuracy value threshold Nmax; and applying the maximum accuracy value threshold Nmax to the score of the characteristic quantity associated with the performance of the reference task by a current test subject to discriminate the score on the basis of the threshold Nmax and determine in which one of the first and second groups that the score of the characteristic quantity associated with the performance of the reference task is grouped as a representation of the motor function and cognitive function of a current test subject.

* * * * *